US008598231B2

(12) United States Patent
Fenyvesi et al.

(10) Patent No.: US 8,598,231 B2
(45) Date of Patent: *Dec. 3, 2013

(54) FLAVORING AGENTS CONTAINING BIO-DERIVED 1,3-PROPANEDIOL AND ITS CONJUGATE ESTERS

(71) Applicant: DuPont Tate & Lyle Bio Products Company, LLC, Wilmington, DE (US)

(72) Inventors: Gyorgyi Fenyvesi, Wilmington, DE (US); Melissa Joerger, Newark, DE (US); Robert Miller, Wilmington, DE (US); Ann Wehner, Hockessin, DE (US)

(73) Assignee: DuPont Tate & Lyle Bio Products Company, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/834,000

(22) Filed: Mar. 15, 2013

(65) Prior Publication Data

US 2013/0210934 A1 Aug. 15, 2013

Related U.S. Application Data

(63) Continuation of application No. 13/238,776, filed on Sep. 21, 2011, now Pat. No. 8,436,046, which is a continuation of application No. 12/786,506, filed on May 25, 2010, now Pat. No. 8,048,920, which is a continuation of application No. 11/705,198, filed on Feb. 12, 2007, now Pat. No. 7,759,393.

(60) Provisional application No. 60/772,471, filed on Feb. 10, 2006, provisional application No. 60/772,194, filed on Feb. 10, 2006, provisional application No. 60/772,193, filed on Feb. 10, 2006, provisional application No. 60/772,111, filed on Feb. 10, 2006, provisional application No. 60/772,120, filed on Feb. 10, 2006, provisional application No. 60/772,110, filed on Feb. 10, 2006, provisional application No. 60/772,112, filed on Feb. 10, 2006, provisional application No. 60/846,948, filed on Sep. 25, 2006, provisional application No. 60/853,920, filed on Oct. 24, 2006, provisional application No. 60/859,264, filed on Nov. 15, 2006, provisional application No. 60/872,705, filed on Dec. 4, 2006, provisional application No. 60/880,824, filed on Jan. 17, 2007.

(51) Int. Cl.
*A61K 31/22* (2006.01)
*A61K 31/23* (2006.01)
*A61K 31/045* (2006.01)

(52) U.S. Cl.
USPC .......................... 514/546; 514/552; 514/724

(58) Field of Classification Search
USPC ........................ 514/546, 552, 724
See application file for complete search history.

(56) References Cited

U.S. PATENT DOCUMENTS

| | | |
|---|---|---|
| 4,404,184 A | 9/1983 | Pittet et al. |
| 5,286,512 A | 2/1994 | Klemann et al. |
| 5,633,362 A | 5/1997 | Nagarajan et al. |
| 5,686,276 A | 11/1997 | Laffend et al. |
| 5,821,092 A | 10/1998 | Nagarajan et al. |
| 6,025,184 A | 2/2000 | Laffend et al. |
| 6,136,576 A | 10/2000 | Diaz-Torres et al. |
| 6,358,716 B1 | 3/2002 | Bulthuis et al. |
| 6,361,983 B1 | 3/2002 | Ames |
| 6,406,895 B1 | 6/2002 | Defretin et al. |
| 6,428,767 B1 | 8/2002 | Burch et al. |
| 6,479,716 B2 | 11/2002 | Hilaly et al. |
| 6,551,640 B1 | 4/2003 | Drantch et al. |
| 6,555,700 B1 | 4/2003 | Horrobin et al. |
| 6,576,340 B1 | 6/2003 | Sun et al. |
| 6,726,887 B1 | 4/2004 | Sugarman |
| 7,098,368 B2 | 8/2006 | Seapan et al. |
| 7,759,393 B2 * | 7/2010 | Joerger et al. .................. 514/546 |
| 8,048,920 B2 * | 11/2011 | Joerger et al. .................. 514/546 |
| 8,436,046 B2 * | 5/2013 | Fenyvesi et al. ............... 514/546 |
| 2003/0228395 A1 | 12/2003 | Garti et al. |
| 2004/0105899 A1 | 6/2004 | Dowdle et al. |
| 2005/0020805 A1 | 1/2005 | Sunkara et al. |
| 2005/0069997 A1 | 3/2005 | Adkesson et al. |
| 2005/0154114 A1 | 7/2005 | Hale |
| 2006/0035808 A1 | 2/2006 | Ahmed et al. |
| 2006/0110810 A1 | 5/2006 | Rajgarhia et al. |
| 2006/0148053 A1 | 7/2006 | Emptage et al. |
| 2007/0107080 A1 | 5/2007 | Liao et al. |
| 2008/0166448 A1 | 7/2008 | Wittorff et al. |

FOREIGN PATENT DOCUMENTS

| | | |
|---|---|---|
| EP | 1551375 | 2/2007 |
| JP | 2002-138069 | 5/2002 |
| RU | 2146478 | 3/2000 |
| WO | WO 2007/073903 | 7/2007 |

OTHER PUBLICATIONS

"Industrial Bioproducts: Today and Tomorrow" (Paster et al.) Prepared by Energetics, Inc. for the US Department of Energy, Jul. 2003, See p. 1 and 2, Table 1-1 and 1-6.

Huang, et al. "Production of 1,3-Propanediol by *Klebsiella pneumoniae*", Applied Biochemistry and Biotechnology, vols. 98-100, 2002, pp. 687-698.

Fung, et al., "Evolution of Carbon Sinks in a Changing Climate", PNAS, Aug. 9, 2005, vol. 12, No. 32, pp. 11201-11206.

Jabrane, et al., "Study of the Thermal Behaviour of 1,3-Propanediol and its Aqueous Solutions", Thermochimica Acta, 311 (1998), pp. 121-127.

(Continued)

*Primary Examiner* — Raymond Henley, III
(74) *Attorney, Agent, or Firm* — McCarter & English

(57) ABSTRACT

Biodegradable flavoring agent compositions comprising 1,3-propanediol are provided, and the 1,3-propanediol in the composition is biologically derived. The compositions exhibit a lower anthropogenic $CO_2$ emission profile. Also provided are biodegradable flavoring agent compositions comprising an ester of 1,3-propanediol. In these compositions, the ester can have at least 3% biobased carbon.

18 Claims, No Drawings

(56) References Cited

OTHER PUBLICATIONS

Chaudhari, et al., "Diol-esters—A Family of Potential Plant Growth Regulators", Proc. Indian Acad. Sci. (Plant Sci.) vol. 96, No. 5, Nov. 1986, pp. 393-400.

Chen, et al., "Cyclization During Polyesterifications: Isolation of an 18-Member Ring Compound from Reaction of Phthalic Anhydride with 2,2-Dimethyl-1,3-Propanediol", Journal of Applied Polymer Science, 1990, vol. 41, Issue 9-10, pp. 2517-2520.

* cited by examiner

FLAVORING AGENTS CONTAINING BIO-DERIVED 1,3-PROPANEDIOL AND ITS CONJUGATE ESTERS

CROSS REFERENCE TO RELATED APPLICATIONS

This application is a Continuation of U.S. patent application Ser. No. 13/238,776, filed Sep. 21, 2011, now U.S. Pat. No. 8,436,046 which is a Continuation of U.S. patent application Ser. No. 12/786,506, filed on May 25, 2010, now U.S. Pat. No. 8,048,920 which is a Continuation of U.S. patent application Ser. No. 11/705,198, filed on Feb. 12, 2007, now U.S. Pat. No. 7,759,393, which claims the benefit of U.S. Provisional Application Ser. No. 60/772,471, filed Feb. 10, 2006, now expired; U.S. Provisional Application No. 60/772,194, filed Feb. 10, 2006, now expired, U.S. Provisional Application No. 60/772,193, filed Feb. 10, 2006, now expired, U.S. Provisional Application No. 60/772,111, filed Feb. 10, 2006, now expired, U.S. Provisional Application No. 60/772,120, filed Feb. 10, 2006, now expired, U.S. Provisional Application No. 60/772,110, filed Feb. 10, 2006, now expired, U.S. Provisional Application No. 60/772,112, filed Feb. 10, 2006, now expired, U.S. Provisional Application No. 60/846,948, filed Sep. 25, 2006, now expired, U.S. Provisional Application No. 60/853,920, filed Oct. 24, 2006, now expired, U.S. Provisional Application No. 60/859,264, filed Nov. 15, 2006, now expired, U.S. Provisional Application No. 60/872,705, filed Dec. 4, 2006, now expired and U.S. Provisional Application No. 60/880,824, filed Jan. 17, 2007, now expired, the disclosures of which are expressly incorporated herein by reference in their entireties.

FIELD OF THE INVENTION

The invention relates to biodegradable flavoring agent compositions comprising 1,3-propanediol, 1,3-propanediol ester, or combinations thereof.

BACKGROUND OF THE INVENTION

Consumers and manufacturers are increasingly concerned with the environmental impact of all products. The effort towards environmental impact awareness is a universal concern, recognized by government agencies. The Kyoto Protocol amendment to the United Nations Framework Convention on Climate Change (UNFCCC) currently signed by 156 nations is one example of a global effort to favor safer environmental manufacturing over cost and efficiency. Especially when applied to goods like, personal care, cosmetics, therapeutics and cosmeceuticals, consumers are increasingly selective about the origins of the products they purchase. The 2004 Co-operative Bank's annual Ethical Consumerism Report (www.co-operativebank.co.uk) disclosed a 30.3% increase in consumer spending on ethical retail products (a general classification for environmental safe, organic and fair trade goods) between 2003 and 2004, while total consumer spending during the same period rose only 3.7%.

One of the single greatest environmental concerns to consumers is the global warming effect and greenhouse gases that contribute to the effect. Greenhouse gases are gases that allow sunlight to enter the atmosphere freely. When sunlight strikes the Earth's surface, some of it is reflected back towards space as infrared radiation. Greenhouse gases absorb this infrared radiation and trap the heat in the atmosphere. Over time, the amount of energy sent from the sun to the Earth's surface should be about the same as the amount of energy radiated back into space, leaving the temperature of the Earth's surface roughly constant. However, increasing the quantity of greenhouse gases above the quantity that existed before the rise of human industrialization is thought to increase the retained heat on the Earth's surface and produce the global warming observed in the last two centuries.

Carbon dioxide is singled out as the largest component of the collection of greenhouse gases in the atmosphere. The level of atmospheric carbon dioxide has increased 50% in the last two hundred years. Any further addition of carbon dioxide to the atmosphere is thought to further shift the effect of greenhouse gases from stabilization of global temperatures to that of heating. Consumers and environmental protection groups alike have identified industrial release of carbon into the atmosphere as the source of carbon causing the greenhouse effect. Only organic products composed of carbon molecules from renewably based sources such as plant sugars and starches and ultimately atmospheric carbon are considered to not further contribute to the greenhouse effect, when compared to the same organic molecules that are petroleum or fossil fuel based.

In addition to adding carbon dioxide to the atmosphere, current methods of industrial production of propanediols produce contaminants and waste products that include among them sulfuric acid, hydrochloric acid, hydrofluoric acid, phosphoric acid, tartaric acid, acetic acids, Alkali metals, alkaline earth metals, transitional metals and heavy metals, including Iron, cobalt, nickel, copper, silver, molybdenum, tungsten, vanadium, chromium, rhodium, palladium, osmium, iridium, rubidium, and platinum (U.S. Pat. Nos. 2,434,110, 5,034,134, 5,334,778, and 5,10,036).

There is a need for all manufactures to provide products reduced environmental impacts, and to especially consider the carbon load on the atmosphere. There is also an environmental advantage for manufacturers to provide products of renewably based sources. Further, there is a need for a proven solvent which is produced with no or little increase to the present carbon-dioxide level in the environment.

Published U.S. Patent Application No. 2005/0069997 discloses a process for purifying 1,3-propanediol from the fermentation broth of a cultured *E. coli* that has been bioengineered to synthesize 1,3-propanediol from sugar. The basic process entails filtration, ion exchange and distillation of the fermentation broth product stream, preferably including chemical reduction of the product during the distillation procedure. Also provided are highly purified compositions of 1,3-propanediol.

Personal care, animal care, cosmetic, therapeutic, pharmaceutic, nutraceutic, aromatherapy, fragrance and cosmeceutic formulations benefit from glycols in the compositions as, for example, surfactants, humectants, solvents, neutralizers, emulsifiers, preservatives and/or fragrance enhancers and fixatives. Typically the glycol component in personal care applications include propylene glycol, 1,3-butylene glycol, or 2-methyl-1,3-propanediol. Because of production costs and relative low purity, conventional 1,3-propanediol, though exhibiting properties equal to if not better than the aforementioned glycols, generally is not used in such compositions.

Moreover, in the context of personal care, animal care, cosmetic, therapeutic, pharmaceutic, nutraceutic, aromatherapy, fragrance and cosmeceutic formulations incorporating a botanical, vegetal, protein/peptide, marine, algae or milk extract, or fragrance concentrate or oil, consumers pay attention to the quality and environmental impact of the product. Currently, botanical, vegetal, protein/peptide, marine, algae and milk extracts, and fragrance concentrates utilize chemical solvents, such as propylene glycol, 2-methyl-1,3- propanediol, butylene glycol, dipropylene glycol, synthetic glycerin, and ethanol, for the extraction process. In many cases these chemical solvents are used in combination with each other. Despite the fact these chemicals are suitable solvents, they have an intrinsic disadvantage because they represent a petroleum-based component of an otherwise "all natural" product. Additionally, safety assessments of these solvents provide evidence that they can cause skin irritation. (Cosmetic Ingredient Review Expert Panel (1994) Final Report on the Safety Assessment of Propylene Glycol and Polypropylene Glycols. J. Am. College Toxicol., 13(6):437-491).

Essential oils extracted from plants are widely used cosmetic and personal care formulations. Colors extracted from plants are used in the food and non-food-industry. Medicinal plant extractions are being used for the treatment various disorders. Though several methods can be used for extraction of flavors, fragrances, colors, and active ingredients, solvent extraction is one of widely used method. Selective extraction of required ingredients, stability of the extracted ingredients, and separation of ingredients from unwanted solvents are key factors for extraction. When volatile solvents such as ethanol used for extraction of active ingredients, they need to be removed before using the ingredients in formulations. When solvents are removed some of the active ingredients may not be stable and decompose.

SUMMARY OF THE INVENTION

Detergent compositions comprising 1,3-propanediol are provided, and the 1,3-propanediol in the composition is biologically derived. Also provided are detergent compositions comprising an ester of 1,3-propanediol. In these compositions, the ester can have at least 3% biobased carbon.

DETAILED DESCRIPTION

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Solvents for diluting and extracting natural extracts are often synthetic, petroleum based organic solvents. Botanical, vegetal, protein/peptide, marine, algae, and milk extracts, also known as an essential oils, are an attractive component in many compositions. These essential oils impart aromatics, active ingredients, and other functionalities such as hand-feel, softening, emolliency, healing, cooling, refreshing, antimicrobial, astringency, nail-strengthening, promotion of healthy skin tissue and hair, cleansing, stimulating, whitening, delivery of anti-oxidants and skin-soothing attributes to a product. Essential oils are the volatile oils of plant/vegetal, protein/peptide, lipid, marine, algae or milk materials that have been removed either by distillation or solvent extraction.

Biologically-derived 1,3-propanediol and its conjugate esters can be used as a solvent to extract essential oils and other extracts from extract sources. Bio-derived 1,3-propanediol and its conjugate esters can be used as a solvent system for botanical extracts and fragrance concentrates and oils at a 10% to approaching 100% concentration range.

Additionally, biologically-derived 1,3-propanediol and its conjugate esters can be used as a solvent to dilute or solubilize extracts in compositions. Biologically-derived 1,3-propanediol and its conjugate esters are unique as solvents in that they are naturally derived, and therefore attractive to consumers who avoid synthetic chemicals.

Biologically-derived 1,3-propanediol and its conjugate esters provide for non-irritating solvents for the extraction and dilution of botanicals, vegetal, protein/peptide, marine, algae, milk substrates or fragrance concentrates and oils. In an aspect of the invention the solvent is composed of all natural components, the term "all natural" as used herein refers to a product that is manufactured from ingredients that are natural occurring. Specifically, biologically derived 1,3-propanediol comprises non-petroleum based carbon.

The conjugate esters of biologically-derived 1,3-propanediol discussed herein include the mono and diesters of biologically derived 1,3-propanediol.

Biologically-derived 1,3-propanediol or its ester conjugates are employed as chemical solvents for extraction or diluent of a botanical extract or fragrance concentrate or oil. The process of extracting an extract from a source comprises: (a) providing 1,3-propanediol, an ester of 1,3-propanediol, or a mixture thereof; (b) mixing the 1,3-propanediol, the ester of 1,3-propanediol, or the mixture thereof with the source, which extracts the extract from the source into the ester; and (c) separating the source from the extract and 1,3-propanediol, the ester of 1,3-propanediol, or the mixture thereof.

The process of extraction involves use of a dried substrate such as plant material which is macerated with solvent. Maceration is the most common and economically important technique for extracting aromatics in the modern perfume industry. In this method, raw materials are submerged in a solvent that can dissolve the desired aromatic or other extract compounds. Maceration lasts between fractions of an hour to months. Maceration is often used to extract fragrant compounds from woody or fibrous materials, as well as animal sources. This technique is also useful to extract odorants that are too volatile for distillation or easily denatured by heat.

Alternatively the solvent can be percolated though the substrate material until sufficient soluble materials have leached from the biomass or substrate. The substrate debris is separated from the extract by straining, filtering, or centrifugation.

Another technique for extracting compounds from a raw material is supercritical fluid extraction. This technique uses low heat to reduce degradation of the extract compounds. Supercritical $CO_2$ can be used in this extraction technique.

Extraction can be performed in accordance with the invention by other extraction techniques as well, including distillation. Biologically-derived 1,3-propanediol and its conjugate esters can be used as solvents in distillation extractions. In this technique, commonly used to obtain aromatic compounds from plants, such as orange blossoms and roses, the raw material is heated and the fragrant compounds are recollected through condensation of the distilled vapor. Distillation methods include steam distillation, in which steam is used to drive out volatile fragrant compounds from plant material, leaving a condensate which is called a hydrosol. Distillation also includes dry or destructive distillation where the raw material is heated without a carrier solvent. In this case, biologically-derived 1,3-propanediol and its conjugate esters are used as a solvent to dilute the fragrant compounds after extraction.

In yet another method of extraction, known as expression, raw material is physically squeezed or compressed and the extruded oils are collected. This method is known as extraction and is most commonly performed to extract compounds from the peels of fruits in the citrus family, as these sources contain sufficient oils to make this method feasible. Enfleurage is another extraction method appropriate for use with biologically derived 1,3-propanediol, its conjugate esters, or mixtures thereof.

Biologically derived 1,3-propanediol and its conjugate esters are useful as a solvents for extractions, and as a component in compositions comprising botanical extracts. Botanical sources include, but are not limited to all plants, seeds, stems, roots, flowers, leaves, pollen, spices, and oils. One type of extract appropriate for extraction or dilution is the herbal extract.

An herbal extract is a liquid solution of herbs and solvent. The dried or fresh herbs are combined with solvent, then the solid matter is removed leaving only the oils of the herbs mixed with the solvent. This process is called extraction, and the process produces an herbal extract.

Herbal extracts are sold as dietary supplements and alternative medicine and commonly used for flavoring in baking, cooking or in beverages. They are also used in personal care products such as skin and hair products.

A small amount of the carbon dioxide in the atmosphere is radioactive. This 14C carbon dioxide is created when nitrogen is struck by an ultra-violet light produced neutron, causing the nitrogen to lose a proton and form carbon of molecular weight 14 which is immediately oxidized in carbon dioxide. This radioactive isotope represents a small but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide which is released back to the atmosphere. Virtually all forms of life on Earth depend on this green plant production of organic molecule to produce the chemical energy that facilitates growth and reproduction. Therefore, the 14C that exists in the atmosphere becomes part of all life forms, and their biological products. These renewably based organic molecules that biodegrade to CO2 do not contribute to global warming as there is no net increase of carbon emitted to the atmosphere. In contrast, fossil fuel based carbon does not have the signature radiocarbon ratio of atmospheric carbon dioxide.

Assessment of the renewably based carbon in a material can be performed through standard test methods. Using radiocarbon and isotope ratio mass spectrometry analysis, the biobased content of materials can be determined. ASTM International, formally known as the American Society for Testing and Materials, has established a standard method for assessing the biobased content of materials. The ASTM method is designated ASTM-D6866.

The application of ASTM-D6866 to derive a "biobased content" is built on the same concepts as radiocarbon dating, but without use of the age equations. The analysis is performed by deriving a ratio of the amount of radiocarbon (14C) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of Biomass material present in the sample.

The modern reference standard used in radiocarbon dating is a NIST (National Institute of Standards and Technology) standard with a known radiocarbon content equivalent approximately to the year AD 1950. AD 1950 was chosen since it represented a time prior to thermo-nuclear weapons testing which introduced large amounts of excess radiocarbon into the atmosphere with each explosion (termed "bomb carbon"). The AD 1950 reference represents 100 pMC.

"Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. It's gradually decreased over time with today's value being near 107.5 pMC. This means that a fresh biomass material such as corn could give a radiocarbon signature near 107.5 pMC.

Combining fossil carbon with present day carbon into a material will result in a dilution of the present day pMC content. By presuming 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A biomass content result is derived by assigning 100% equal to 107.5 pMC and 0% equal to 0 pMC. In this regard, a sample measuring 99 pMC will give an equivalent biobased content result of 93%.

Assessment of the materials described herein were done in accordance with ASTM-D6866. The mean values quoted in this report encompasses an absolute range of 6% (plus and minus 3% on either side of the biobased content value) to account for variations in end-component radiocarbon signatures. It is presumed that all materials are present day or fossil in origin and that the desired result is the amount of biobased component "present" in the material, not the amount of biobased material "used" in the manufacturing process.

"Substantially purified," as used by applicants to describe the biologically-produced 1,3-propanediol produced by the process of the invention, denotes a composition comprising 1,3-propanediol having at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm.

A "b*" value is the spectrophotometrically determined "Yellow Blue measurement as defined by the CIE L*a*b* measurement ASTM D6290.

The abbreviation "AMS" refers to accelerator mass spectrometry.

The abbreviation "IRMS" refers to measurements of $CO_2$ by high precision stable isotope ratio mass spectrometry.

"Biologically produced" means organic compounds produced by one or more species or strains of living organisms, including particularly strains of bacteria, yeast, fungus and other microbes. "Bio-produced," "biologically-derived" and "biologically produced" are used synonymously herein. Such organic compounds are composed of carbon from atmospheric carbon dioxide converted to sugars and starches by green plants.

"Biologically-based" means that the organic compound is synthesized from biologically produced organic components. It is further contemplated that the synthesis process disclosed herein is capable of effectively synthesizing other monoesters and diesters from bio-produced alcohols other than 1,3-propanediol; particularly including ethylene glycol, diethylene glycol, triethylene glycol, –, dipropylene glycol, tripropylene diol, 2-methyl 1,3-propanediol, neopentyl glycol and bisphenol A. "Bio-based", and "bio-sourced"; "biologically derived"; and "bio-derived" are used synonymously herein.

"Carbon of atmospheric origin" as used herein refers to carbon atoms from carbon dioxide molecules that have recently, in the last few decades, been free in the earth's atmosphere. Such carbons in mass are identifiable by the present of particular radioisotopes as described herein. "Green carbon", "atmospheric carbon", "environmentally friendly carbon", "life-cycle carbon", "non-fossil fuel based carbon", "non-petroleum based carbon", "carbon of atmospheric origin", and "biobased carbon" are used synonymously herein.

"Flavoring agents" are substances added to foods, beverages, cosmetics, pharmaceuticals, or medicines to improve the quality of the taste if such compositions. Oils, such as orange oils are considered flavoring agents.

An aspect of the invention is use of biologically-derived 1,3-propanediol or its ester conjugate to prepare a flavoring agent, for example by treating a flavoring oil with biologically-derived 1,3-propanediol or its ester conjugate.

Compositions in accordance with the invention include a composition comprising an ester of 1,3-propanediol and an extraction product. The esters can be a varying amount of biobased carbon depending on the compound used in the esterification. Biologically derived 1,3-propanediol contains biobased carbon. All three carbon atoms in 1,3 propanediol are biobased carbons. If the conjugate esters are formed using carboxylic acids that contain all biobased carbon, then the resulting esters also contain all biobased carbon. If, however, the carboxylic acids contain non-biobased carbons, i.e. carbons from a fossil fuel source, then the resulting ester will contain a percentage of biobased carbon in proportion to the number of carbons contributed from the carboxylic acid compared to the three carbons contributed from the biologically-derived 1,3-propanediol.

For example, distearate propanediol contains 39 carbon atoms, 18 from each of the stearic acid carbon chains and three from the 1,3-propanediol. Accordingly, if the stearic acid is non-biobased, 36 carbons out of the total 39 in distearate propanediol are non-biobased carbon. The predicted bio-based content of distearate propanediol made from biologically-derived propanediol, and non-biologically derived strearic acid is 7.7 percent.

In an analysis performed using the ASTM-D6866 method, propylene glycol dibenzoate (BENZOFLEX (R) 284, Velsicol Chem. Corp. Rosemont, Ill.) was found to have 0% bio-based carbon content. The same analysis of propanediol dibenzoate, synthesized using biologically-derived 1,3-propanediol had 19% bio-based carbon content. The predicted bio-based carbon content propanediol dibenzoate made from biologically-derived 1,3 propanediol is 17.6%, which is within the standard deviation of the method.

If the stearic acid in the above example is biobased, the resulting distearate propanediol would have a biobased content of 100%. Accordingly, the conjugate esters of biologically-derived 1,3-propanediol have biobased content values proportional to the biobased content of the acids used to form the esters. The esters therefore can have biobased content of at least 3% biobased carbon, at least 6% biobased carbon, at least 10% biobased carbon, at least 25% biobased carbon, at least 50% biobased carbon, at least 75% biobased carbon, and 100% biobased carbon.

The compositions comprising an extract and a conjugate ester of 1,3-propanediol can be between about 0.1% and about 5% ester, between about 0.5% and about 25% ester, between about 25% and about 50% ester, between about 50% and about 75% ester, and between about 75% and about 99% ester, and between 99% and about 100% ester.

Compositions in accordance with the invention also include compositions comprising 1,3-propanediol and an extract. The 1,3-propanediol of these compositions has at least 95% biobased carbon, or alternatively, the 1,3-propanediol has 100% biobased carbon. The compositions comprising an extract and 1,3-propanediol can be between about 0.1% and about 5% 1,3-propanediol, between about 0.5% and about 25% 1,3-propanediol, between about 25% and about 50% 1,3-propanediol, between about 50% and about 75% 1,3-propanediol, and between about 75% and about 99% 1,3-propanediol.

Compositions in accordance with the invention also include compositions comprising both 1,3-propanediol and a conjugate ester of 1,3-propanediol along with an extract. The 1,3-propanediol of these compositions has at least 95% biobased carbon, or alternatively, the 1,3-propanediol has 100% biobased carbon. The compositions comprising an extract and a mixture of 1,3-propanediol and a conjugate ester of 1,3-propanediol can be between about 0.1% and about 5% mixture, between about 0.5% and about 25% mixture, between about 25% and about 50% mixture, between about 50% and about 75% mixture, and between about 75% and about 99% mixture.

A mixture of a glycol and ester can be very effective in extractions, and the mixture can remove more active ingredients than either solvent alone. More actives are extracted from plant material using a solvent mixture because the esters (especially diesters) are non-polar, whereas glycol components are polar. Accordingly, the lipophilic ingredients can easily be removed from the plants using the ester glycol mixture. In some cases the density of an ester can be much higher than the density of the glycol, and after the maceration process the "cake" (the extract of the ester) can easily solidify and separate from the glycol phase. Additionally, the esters can be volatile compounds and in extractions the esters can be easily evaporated to obtain concrete, fragrance oil, absolute, or enfleurage.

The 1,3-propanediol, the conjugate esters of 1,3-propanediol, and mixtures thereof can be effective as solvents and diluents when combined with other appropriate solvents, including water.

Biologically-Derived 1,3-propanediol

The present invention relates to compositions comprising a botanical, vegetal, protein/peptide, marine, algae, or milk extract or fragrance concentrate or oil wherein biologically-derived 1,3-propanediol or its ester conjugate is employed as a chemical solvent for extraction or diluent of the botantical, vegetal, protein/peptide, marine, algae, or milk extract or fragrance concentrate or oil. "Biologically-derived" means that the 1,3-propanediol is synthesized by one or more species or strains of living organisms, including particularly strains of bacteria, yeast, fungus and other microbes. Biologically-derived 1,3-propanediol useful in shampoo or body wash compositions disclosed herein.

Biologically-derived 1,3-propanediol is collected in a high purity form. Such 1,3-propanediol has at least one of the following characteristics: 1) an ultraviolet absorption at 220 nm of less than about 0.200 and at 250 nm of less than about 0.075 and at 275 nm of less than about 0.075; or 2) a composition having L*a*b* "b*" color value of less than about 0.15 and an absorbance at 270 nm of less than about 0.075; or 3) a peroxide composition of less than about 10 ppm; or 4) a concentration of total organic impurities of less than about 400 ppm. A "b*" value is the spectrophotometrically determined Yellow Blue measurement as defined by the CIE L*a*b* measurement ASTM D6290.

The level of 1,3-propanediol purity can be characterized in a number of different ways. For example, measuring the remaining levels of contaminating organic impurities is one useful measure. Biologically-derived 1,3-propanediol can have a purity level of less than about 400 ppm total organic contaminants; preferably less than about 300 ppm; and most preferably less than about 150 ppm. The term ppm total organic purity refers to parts per million levels of carbon-containing compounds (other than 1,3-propanediol) as measured by gas chromatography.

Biologically-derived 1,3-propanediol can also be characterized using a number of other parameters, such as ultraviolet light absorbance at varying wavelengths. The wavelengths 220 nm, 240 nm and 270 nm have been found to be useful in determining purity levels of the composition. Biologically-derived 1,3-propaediol can have a purity level wherein the UV absorption at 220 nm is less than about 0.200 and at 240 nm is less than about 0.075 and at 270 nm is less than about 0.075.

Biologically-derived 1,3-propanediol can have a b* color value (CIE L*a*b*) of less than about 0.15.

The purity of biologically-derived 1,3-propanediol compositions can also be assessed in a meaningful way by measuring levels of peroxide. Biologically-derived 1,3-propanediol can have a concentration of peroxide of less than about 10 ppm.

It is believed that the aforementioned purity level parameters for biologically-derived and purified 1,3-propanediol (using methods similar or comparable to those disclosed in U.S. Patent Application No. 2005/0069997) distinguishes such compositions from 1,3-propanediol compositions prepared from chemically purified 1,3-propanediol derived from petroleum sources.

1,3-propanediol produced biologically via fermentation is known, including in U.S. Pat. No. 5,686,276, U.S. Pat. No. 6,358,716, and U.S. Pat. No. 6,136,576, which disclose a process using a recombinantly-engineered bacteria that is able to synthesize 1,3-propanediol during fermentation using inexpensive green carbon sources such as glucose or other sugars from plants. These patents are specifically incorporated herein by reference. Biologically-derived 1,3-propanediol can be obtained based upon use of the fermentation broth generated by a genetically-engineered *Eschericia coli* (*E. coli*), as disclosed in U.S. Pat. No. 5,686,276. Other single organisms, or combinations of organisms, may also be used to biologically produce 1,3-propanediol, using organisms that have been genetically-engineered according to methods known in the art. "Fermentation" refers to a system that catalyzes a reaction between substrate(s) and other nutrients to product(s) through use of a biocatalyst. The biocatalysts can be a whole organism, an isolated enzyme, or any combination or component thereof that is enzymatically active. Fermentation systems useful for producing and purifying biologically-derived 1,3-propanediol are disclosed in, for example, Published U.S. Patent Application No. 2005/0069997 incorporated herein by reference.

The transformed *E. coli* DH5α containing cosmid pKP1 containing a portion of the *Klebsiella* genome encoding the glycerol dehydratase enzyme was deposited on 18 Apr. 1995 with the ATCC under the terms of the Budapest Treaty and is identified by the ATCC number ATCC 69789. The transformed *E. coli* DH5α containing cosmid pKP4 containing a portion of the *Klebsiella* genome encoding a diol dehydratase enzyme was deposited on 18 Apr. 1995 with the ATCC under the terms of the Budapest Treaty and is identified by the ATCC number ATCC 69790. As used herein, "ATCC" refers to the American Type Culture Collection international depository located at 10801 University Boulevard, Manassas, Va., 20110 2209, U.S.A. The "ATCC No." is the accession number to cultures on deposit with the ATCC.

The biologically derived 1,3-propanediol (bio-PDO) for use in the current invention, produced by the process described herein, contains carbon from the atmosphere incorporated by plants, which compose the feedstock for the production of bio-PDO. In this way, the bio-PDO contains only renewable carbon, and not fossil fuel based, or petroleum based carbon. Therefore the use of bio-PDO and its conjugate esters has less impact on the environment as the propanediol does not deplete diminishing fossil fuels. The use of the use of bio-PDO and its conjugate esters also does not make a net addition of carbon dioxide to the atmosphere, and thus does not contribute to greenhouse gas emissions. Thus, the present invention can be characterized as more natural and having less environmental impact than similar compositions comprising petroleum based glycols.

Moreover, as the purity of the bio-PDO utilized in the compositions of the invention is higher than chemically synthesized PDO and other glycols, risk of introducing impurities that may cause irritation is reduced by its use over commonly used glycols, such as propylene glycol.

In one embodiment of the invention, a composition comprising 1,3-propanediol and an extraction product is provided, where the 1,3-propanediol is biologically derived. The biologically-derived 1,3-propanediol can have at least 85% biobased carbon, at least 95% biobased carbon, or 100% biobased carbon, when assessed by the application of ASTM-D6866 as described above.

A sample of biologically-derived 1,3-propanediol was analysized using ASTM method D 6866-05. The results received from Iowa State University demonstrated that the above sample was 100% bio-based content. In a separate analysis, also performed using a ASTM-D6866 method, chemical, or petroleum-based 1,3-propanediol (purchased from SHELL) was found to have 0% bio-based content. Propylene glycol (USP grade from ALDRICH) was found to have 0% bio-based content.

It is contemplated herein that other renewably-based or biologically-derived glycols, such as ethylene glycol or 1,2 propylene glycol, diethylene glycol, triethylene glycol among others, can be used in the extractions or compositions of the present invention.

There may be certain instances wherein the extractions or extract compositions of the invention may comprise a combination of a biologically-derived 1,3-propanediol and one or more non biologically-derived glycol components, such as, for example, chemically synthesized 1,3-propanediol. In such occasions, it may be difficult, if not impossible to determine which percentage of the glycol composition is biologically-derived, other than by calculating the bio-based carbon content of the glycol component. In this regard, in the extraction solvents and extract compositions of the invention, the 1,3-propanediol used as a solvent, or used to form 1,3 propanediol esters, can comprise at least about 1% bio-based carbon content up to 100% bio-based carbon content, and any percentage there between.

Ester Conjugates of Biologically Derived 1,3-Propanediol

Esters of biologically derived 1,3-propanediol, "bio-PDO" can be synthesized by contacting bio-PDO with an organic acid. The organic acid can be from any origin, preferably either a biosource or synthesized from a fossil source. Most preferably the organic acid is derived from natural sources or bio-derived having formula $R_1R_2$—COOH. Where in the substituent $R_1$ can be saturated or unsaturated, substituted or unsubstituted, aliphatic or aromatic, linear or branched hydrocarbon having chain length 1 to 40 or their salts or alkyl esters. Where in the substituent $R_2$ can be H or COOH. The hydrocarbon chain can also have one or more functional groups such as alkene, amide, amine, carbonyl, carboxylic acid, halide, hydroxyl groups. Naturally occurring organic acids produced esters containing all biobased carbon. These naturally occurring organic acids, especially those produced by a biological organism, are classified as bio-produced and the resulting ester or diester could thereby also be classified as bio-produced. Naturally occurring sources of such fatty acids include coconut oil, various animal tallows, lanolin, fish oil, beeswax, palm oil, peanut oil, olive oil, cottonseed oil, soybean oil, corn oil, rape seed oil. Conventional fractionation and/or hydrolysis techniques can be used if necessary to obtain the fatty acids from such materials.

Appropriate carboxylic acids for producing esters of biologically-derived 1,3-propanediol generally include: (1) C1-C3 carbon containing mono carboxylic acids, including formic acid and acetic acid; (2) fatty acids, such as those acids containing four or more carbon atoms; (3) saturated fatty acids, such as butyric acid, caproic acid, valeric acid, caprylic acid, capric acid, lauric acid, myristic acid, palmitic acid, stearic acid, arachidic acid, and behenic acid; (4) unsaturated fatty acids, such as oleic acid, linoleic acid, and euricic acid; (5) polyunsaturated fatty acids, such as alpha-linolenic acid, stearidonic acid (or moroctic acid), eicosatetraenoic acid, omega-6 fatty acids, arachidonic acids, and omega-3 fatty acids, eicosapentaenoic acid (or timnodonic acid), dosocapentaenoic acid (or clupanodonic acid), and docosahexaenoic acid (or cervonic acid); (6) hydroxy fatty acids, such as 2-hydroxy linoleic acid, and recinoleic acid; phenylalkanoic fatty acids, such as 11-phenyl undecanoic acid, 13-phenyl tridecanoid acid, and 15-phenyl tridecanoid acid; and (7) cyclohexyl fatty acids, such as 11-cyclohexyl undecanoic acid, and 13-cyclohexyl tridecanoic acid.

The following acids and their salts or alkyl esters are specifically useful, acetic, butyric, lauric, myristic, palmitic, stearic, arachidic, adipic, benzoic, caprylic, maleic, palmitic, sebacic, archidonic, erucic, palmitoleic, pentadecanoic, heptadecanoic, nondecanoic, octadectetraenoic, eicosatetraenoic, eicosapentaenoic, docasapentaenoic, tetracosapentaenoic, tetrahexaenoic, docosahexenoic, (alpha)-linolenic, docosahexaenoic, eicosapentaenoic, linoleic, arachidonic, oleic, erucic, formic, prop ionic, valeric, caproic, capric, malonic, succinic, glutaric, adipic, pimelic, suberic, azelaic, tartaric, citri c, salicylic, acetyl-salicylic, pelargonic, behenic, cerotic, margaric, montanic, melissic, lacceroic, ceromelissic, geddic, ceroplastic undecylenic, ricinoleic, and elaeostearic acid as well as mixtures of such acids. A more preferred list of suitable organic acids are acetic, adipic, benzoic, maleic, sebacic, and mixtures of such acids. A more preferred list of suitable "fatty acids" meaning generally acids named containing 8-40 carbon in the carbon useful in the present invention include butyric, valeric, caproic, caprylic, pelargonic, capric, lauric, myristic, palmitic, stearic, arachidic, behenic, cerotic, oleic, linoleic, linolenic, margar ic, montanic, melissic, lacceroic, ceromelissic, geddic, ceroplastic and the mixtures of such acids. Among those acids, these acids, and their salts and alkyl esters are most preferred stearic, lauric, palmetic, oleic, 2-ethyl hexanoic, and 12-hydroxystearic and mixtures of such acids.

The esters produced include all the appropriate conjugate mono and diesters of 1,3 propanediol using the described organic acids. Some esters in particular that are produced include propanediol distearate and monostearate, propanediol dilaurate and monolaurate, propanediol dioleate and monooleate, propanediol divalerate and monovalerate, propanediol dicaprylate and monocaprylate, propanediol dimyristate and monomyristate, propanediol dipalmitate and monopalmitate, propanediol dibehenate and monobehenate, propanediol adipate, propanediol maleate, propanediol dibenzoate, propanediol diacetate, and all mixtures thereof.

In particular, the esters produced include: propanediol distearate and monostearate, propanediol dioleate and monooleate, propanediol dicaprylate and monocaprylate, propanediol dimyristate and monomyristate, and all mixtures thereof.

Generally 1,3-propanediol can be contacted, preferably in the presence of an inert gas reacted with a fatty acid or mixture of fatty acids or salts of fatty acids in the absence or presence of a catalyst or mixture of two or more catalysts, at temperatures ranging from 25° C. to 400° C.

During the contacting, water is formed and can be removed in the inert gas stream or under vacuum to drive the reaction complete. Any volatile byproducts can be removed similarly. When the reaction is complete, the heating can be stopped and cooled.

The catalyst can be removed preferably by dissolving and removing in deionized water. If catalyst can be removed by treating with deionized water, the reaction mixture is treated with aqueous solutions of acid or base to forms salts and removing the salts either by washing or filtering.

Further purification to obtain high purity fatty esters, preferably for pharmaceutical application can be carried out by dissolving in a solvent that dissolves fatty ester easily at higher temperatures and least at lower temperatures and recrystallyzing with or without addition of additional solvent at low temperatures.

The catalyst can be an acid for non-limiting examples, sulfuric acid, or p-toluene sulfonic acid. The catalyst can also be a base, for non-limiting example, sodium hydroxide. The catalyst can also be a salt, for non-limiting example, potassium acetate. The catalyst can also be an alkoxide, for non-limiting example, titanium tetraisopropoxide. The catalyst can also be a heterogeneous catalyst, for non-limiting examples: zeolite, heteropolyacid, amberlyst, or ion exchange resin. The catalyst can also be a metal salt, for non-limiting examples, tin chloride, or copper chloride, The catalyst can also be an enzyme, such as those known in the art. The catalyst can also be an organic acid, for a non-limiting example, formic acid. Finally the catalyst can also be an organometalic compound, for non-limiting example, n-butylstannoic acid.

This process can be carried out in the presence or absence of a solvent. If a solvent is not necessary to facilitate the production of fatty ester, it is preferred that the process is carried out in the absence of solvent.

The process can be carried out at atmospheric pressure or under vacuum or under pressurized conditions.

Reaction 1 (diester)

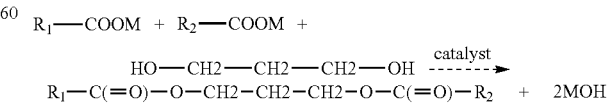

Where $R_1$ and $R_2$ is a hydrocarbon, preferably with a carbon chain length of about 1 to about 40. Such hydrocarbons can be saturated or unsaturated, substituted or unsubstituted, linear or branched
M is hydrogen, an alkali metal or an alkyl group.

Reaction 2 (monoester)

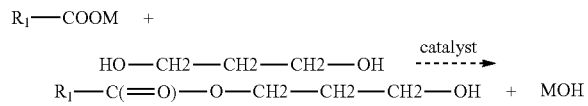

Where $R_1$ is a hydrocarbon, preferably with a carbon chain length of about 1 to about 40. Such hydrocarbons can be saturated or unsaturated, substituted or unsubstituted, linear or branched. M is hydrogen, an alkali metal or an alkyl group.

Compositions in accordance with the invention comprise esters in which R1 has one or more functional groups selected from the group consisting of alkene, amide, amine, carbonyl, carboxylic acid, halide, hydroxyl groups, ether, alkyl ether, sulfate and ethersulfate. The esters can have the formula R1-C(=O)—O—CH2-CH2-CH2-O—C(=O)—R2, wherein both R1 and R2 are linear or branched carbon chains of a length between about 1 an about 40 carbons. R1 and R2 can have one or more functional groups selected from the group consisting of alkene, amide, amine, carbonyl, carboxylic acid, halide, hydroxyl groups, ether, alkyl ether, sulfate and ethersulfate. Additionally, R1 and R2 can be the same carbon chain in the case of a diester.

Any molar ratio of diol to dicarboxylic acid or its salt or its ester can be used. The preferred range of the diol to dicarboxylic acid is from about 1:3 to about 2:1. This ratio can be adjusted to shift the favor of the reaction from monoester production to diester production. Generally, to favor the production of diesters slightly more than about a 1:2 ratio is used; whereas to favor the production of monoesters about a 1:1 ratio is used. In general, if the diester product is desired over the monoester the ratio of diol to dicarboxylic acid can range from about 1.01:2 to about 1.1:2; however if the monoester is desired a range of ratios from about 1.01:1 to about 2:1 is used.

The catalyst content for the reaction can be from 1 ppm to 60 wt % of the reaction mixture, preferably from 10 ppm to 10 wt %, more preferably from 50 ppm to 2 wt % of the reaction mixture.

The product may contain diesters, monoesters or combination diesters and monoesters and small percentage of unreacted acid and diol depending on the reaction conditions. Unreacted diol can be removed by washing with deionized water. Unreacted acid can be removed by washing with deionized water or aqueous solutions having base or during recrystallization.

Any ester of 1,3-propanediol can be made or used in accordance with the present invention. Short, middle and long chain monoesters and diesters of the 1,3-propanediol can be made. Specifically those acids containing between about 1 and about 36 carbons in the alkyl chain can be produced. More specifically, the following monoesters and diesters can be produced: propanediol distearate (monostearate and the mixture), propandiol dilaurate (monolaurate and the mixture), propanediol dioleate (monooleate and the mixture), propanediol divalerate (monovalerate and the mixture), propanediol dicaprylate (monocaprylate and the mixture), propanediol dimyristate (monomyristate and the mixture), propanediol dipalmitate (monopalmitate and the mixture), propanediol dibehenate (monobehenate and the mixture), propanediol adipate, propanediol maleate, propanediol dibenzoate, and propanediol diacetate.

For compositions comprising an extract and 1,3-propanediol, the conjugate esters of 1,3-propanediol, or mixtures thereof, the extract can be a compound or group of compounds that are extracted from a source material. In some applications, the extract is extracted from a natural source, such as a botanical source. Examples of appropriate natural extracts include botanical extracts, vegetal extracts, protein extracts, lipid extracts, marine extracts, algae extracts, and milk extracts.

Botanical sources for extracts include the following list of families of plants and trees: Acanthaceae, Aceraceae, Achariaceae, Achatocarpaceae, Acoraceae, Actinidiaceae, Actiniopteridaceae, Adiantaceae, Adoxaceae, Aegicerataceae, Aetoxicaceae, Agavaceae, Agdestidaceae, Aitoniaceae, Aizoaceae, Akaniaceae, Alangiaceae, Alismataceae, Alliaceae, Alseuosmiaceae, Alstroemeriaceae, Altingiaceae, Alzateaceae, Amaranthaceae, Amaryllidaceae, Amborellaceae, Ampelidaceae, Anacardiaceae, Anarthriaceae, Ancistrocladaceae, Androstachydaceae, Anemiaceae, Angiopteridaceae, Anisophylleaceae, Annonaceae, Anthericaceae, Antoniaceae, Aphyllanthaceae, Apiaceae, Apocynaceae, Aponogetonaceae, Apostasiaceae, Aquifoliaceae, Araceae, Araliaceae, Araucariaceae, Arecaceae, Aristolochiaceae, Asclepiadaceae, Asparagaceae, Asphodelaceae, Aspidiaceae, Aspleniaceae, Asteliaceae, Asteraceae, Asteranthaceae, Asteranthaceae, Asteranthaceae, Asteranthaceae, Aucubaceae, Austrobaileyaceae, Avicenniaceae, Azollaceae, Balanopaceae, Balanophoraceae, Balsaminaceae, Bambuseae, Barringtoniaceae, Basellaceae, Bataceae, Begoniaceae, Berberidaceae, Betulaceae, Bignoniaceae, Bischofiaceae, Bixaceae, Blechnaceae, Bombacaceae, Bonnetiaceae, Boraginaceae, Botrychiaceae, Brassicaceae, Bruniaceae, Brunoniaceae, Buddlejaceae, Burmanniaceae, Burseraceae, Butomaceae, Buxaceae, Byblidaceae, Byttneriaceae, Cabombaceae, Cactaceae, Caesalpiniaceae, Callitrichaceae, Calycanthaceae, Calyceraceae, Campanulaceae, Canellaceae, Cannabidaceae, Cannaceae, Canotiaceae, Capparidaceae, Caprifoliaceae, Cardiopteridaceae, Caricaceae, Carlemanniaceae, Caryocaraceae, Caryophyllaceae, Casuarinaceae, Cayceraceae, Cecropiaceae, Celastraceae, Centrolepidaceae, Cephalotaceae, Cephalotaxaceae, Ceratophyllaceae, Cercidiphyllaceae, Chemopleuriaceae, Chenopodiaceae, Chloanthaceae, Chloranthaceae, Christenseniaceae, Chrysobalanaceae, Cistaceae, Clethraceae, Clusiaceae, Cneoraceae, Cochlospermaceae, Columelliaceae, Combretaceae, Commelinaceae, Compositae, Connaraceae, Conocephalaceae, Convolvulaceae, Coriariaceae, Cornaceae, Corynocarpaceae, Costaceae, Crassulaceae, Crossosomataceae, Crypteroniaceae, Cryptogrammaceae, Cucurbitaceae, Culcitaceae, Cunoniaceae, Cupressaceae, Cyanastraceae, Cyatheaceae, Cycadaceae, Cyclanthaceae, Cyclocheilaceae, Cymodoceaceae, Cynomoriaceae, Cyperaceae, Cypripediaceae, Cyrillaceae, Danaeaceae, Daphniphyllaceae, Datiscaceae, Davalliaceae, Davidsoniaceae, Degeneriaceae, Dennstaedtiaceae, Dialypetalanthaceae, Diapensiaceae, Dichapetalaceae, Dicksoniaceae, Dicrastylidaceae, Didiereaceae, Didymelaceae, Diegodendraceae, Dilleniaceae, Dioscoreaceae, Dipsacaceae, Dipteridaceae, Dipterocarpaceae, Dracaenaceae, Droseraceae, Dryopteridaceae, Dysphaniaceae, Dysphaniaceae, Ebenaceae, Ecdeiocoleaceae, Elaeagnaceae, Elaeocarpaceae, Elaphoglossaceae, Elatinaceae, Empetraceae, Epacridaceae, Ephedraceae, Equisetaceae, Ericaceae, Eriocaulaceae, Erythropalaceae, Erythroxylaceae, Escalloniaceae, Eucommiaceae, Eucryphiaceae, Euphorbiaceae, Eupomatiaceae, Eupteleaceae, Fabaceae, Fagaceae, Flacourtiaceae, Flagellariaceae, Fouquieriaceae, Frankeniaceae, Fumariaceae, Garryaceae, Geissolomataceae, Gentianaceae, Geosiridaceae, Geraniaceae, Gesneriaceae, Ginkgoaceae, Gleicheniaceae, Globulariaceae, Gnetaceae, Goetzeaceae, Gomortegaceae, Goodeniaceae, Goupiaceae, Gramineae, Grammitaceae, Grammitidaceae, Grubbiaceae, Gunneraceae, Guttiferae, Gyrostemonaceae, Haemodoraceae, Haloragaceae, Haloragidaceae, Hamamelidaceae, Heliconiaceae, Helminthostachyaceae, Hemionitidaceae, Hernandiaceae, Heteropyxidaceae, Himantandraceae, Hippocastanaceae, Hippocrateaceae, Hippuridaceae, Hoplestigmataceae, Hostaceae, Humiriaceae, Hydnoraceae, Hydrangeaceae, Hydrocharitaceae, Hydrocotylaceae, Hydrophyllaceae, Hydrostachyaceae, Hymenophyllaceae, Hymenophyllopsidaceae, Hypericaceae, Hypolepidaceae, Hypoxidaceae, Icacinaceae, Idiospermaceae, Illiciaceae, Iridaceae, Isoetaceae, Ixonanthaceae, Juglandaceae, Julianiaceae, Juncaceae, Juncaginaceae, Koeberliniaceae, Krameriaceae, Labiatae, Lacistemataceae, Lactoridaceae, Lamiaceae, Lardizabalaceae, Lauraceae, Lecythidaceae, Leeaceae, Leguminosae, Leitneriaceae, Lemnaceae, Lennoaceae, Lentibulariaceae, Lilaeaceae, Liliaceae, Limnanthaceae, Limnocharitaceae, Linaceae, Lindsaeaceae, Lissocarpaceae, Loasaceae, Lobeliaceae, Loganiaceae, Lomariopsidaceae, Lophosoriaceae, Loranthaceae, Lowiaceae, Loxogrammaceae, Loxsomaceae, Lunulariaceae, Luzuriagaceae, Lycopodiaceae, Lygodiaceae, Lythraceae, Magnoliaceae, Malesherbiaceae, Malpighiaceae, Malvaceae, Marantaceae, Marattiaceae, Marcgraviaceae, Marchantiaceae, Marsileaceae, Martyniaceae, Matoniaceae, Mayacaceae, Medusagynaceae, Medusandraceae, Melastomataceae, Meliaceae, Melianthaceae, Menispermaceae, Menyanthaceae, Metaxyaceae, Mimosaceae, Misodendraceae, Monimiaceae, Moraceae, Moraceae, Moringaceae, Musaceae, Myoporaceae, Myricaceae, Myristicaceae, Myrothamnaceae, Myrsinaceae, Myrtaceae, Najadaceae, Negripteridaceae, Nelumbonaceae, Nepenthaceae, Nephrolepidaceae, Nolanaceae, Nyctaginaceae, Nymphaeaceae, Nyssaceae, Ochnaceae, Octoknemaceae, Olacaceae, Oleaceae, Oleandraceae, Oliniaceae, Onagraceae, Oncothecaceae, Onocleaceae, Ophioglossaceae, Opiliaceae, Orchidaceae, Orobanchaceae, Osmundaceae, Oxalidaceae, Paeoniaceae, Pandaceae, Pandanaceae, Papaveraceae, Parkeriaceae, Passifloraceae, Pedaliaceae, Penaeaceae, Pentaphragmataceae, Pentaphylaceae, Peperomiaceae, Peraceae, Peranemaceae, Periplocaceae, Petrosaviaceae, Philesiaceae, Philydraceae, Phormiaceae, Phrymaceae, Phytolaccaceae, Pinaceae, Piperaceae, Pittosporaceae, Plagiogyriaceae, Plantaginaceae, Platanaceae, Platyzomataceae, Plumbaginaceae, Poaceae, Podocarpaceae, Podophyllaceae, Podostemaceae, Polemoniaceae, Polygalaceae, Polygonaceae, Polypodiaceae, Pontederiaceae, Portulacaceae, Potaliaceae, Potamogetonaceae, Primulaceae, Proteaceae, Psilotaceae, Pteridaceae, Punicaceae, Pyrolaceae, Quiinaceae, Rafflesiaceae, Ranunculaceae, Rapateaceae, Rebouliaceae, Resedaceae, Restionaceae, Rhamnaceae, Rhizophoraceae, Rhoipteleaceae, Rhoipteleaceae, Rhopalocarpaceae, Roridulaceae, Rosaceae, Rubiaceae, Ruscaceae, Rutaceae, Sabiaceae, Saccifoliaceae, Salicaceae, Salvadoraceae, Salviniaceae, Santalaceae, Sapindaceae, Sapotaceae, Sarcolaenaceae, Sarcospermataceae, Sarraceniaceae, Saururaceae, Saxifragaceae, Scheuchzeriaceae, Schisandraceae, Schizaeaceae, Scrophulariaceae, Scyphostegiaceae, Scytopetalaceae, Selaginaceae, Selaginellaceae, Simaroubaceae, Sinopteridaceae, Smilacaceae, Solanaceae, Sonneratiaceae, Sparganiaceae, Sphaerosepalaceae, Sphenostemonaceae, Stachyuraceae, Stackhousiaceae, Staphyleaceae, Stemonaceae, Sterculiaceae, Strasburgeriaceae, Strelitziaceae, Stromatopteridaceae, Strychnaceae, Styracaceae, Symplocaceae, Taccaceae, Taenitidaceae, Tamaricaceae, Taxaceae, Taxodiaceae, Tecophilaeaceae, Tepuianthaceae, Tetracentraceae, Tetragoniaceae, Tetrameristaceae, Theaceae, Theligonaceae, Thelypteridaceae, Theophrastaceae, Thunbergiaceae, Thurniaceae, Thymelaeaceae, Thyrsopteridaceae, Tichodendraceae, Tiliaceae, Tmesipteridaceae, Tovariaceae, Trapaceae, Tremandraceae, Trigoniaceae, Trilliaceae, Triuridaceae, Trochodendraceae, Tropaeolaceae, Turneraceae, Typhaceae, Uapacaceae, Ulmaceae, Urticaceae, Vacciniaceae, Vahliaceae, Valerianaceae, Velloziaceae, Verbenaceae, Violaceae, Vitaceae, Vittariaceae, Vivianiaceae, Vochysiaceae, Welwitschiaceae, Winteraceae, Xanthorrhoeaceae, Xyridaceae, Zamiaceae, Zingiberaceae, Zosteraceae, Zygophyllaceae.

Preferred families of plants and trees include Anacardiaceae Araceae, Balanopaceae, Balsaminaceae, Begoniaceae, Boraginaceae, Buxaceae, Caricaceae, Cucurbitaceae, Clusiaceae, Daphniphyllaceae, Ericaceae, Euphorbiaceae, Fabaceae, Fagaceae, Hippocastanaceae, Hostaceae, Hydrangeaceae, Labiateae, Lilaeaceae, Magnoliaceae, Moringaceae, Myristicaceae, Myrtaceae, Oleaceae, Orchidaceae, Peperomiaceae, Pinaceae, Primulaceae, and Rutaceae.

The preferred species of plants and trees for extract sources include *Achillea millefolium, Aesculus chinensis, Allium sativum, Artemisia apiacea, Astrocaryum murumuru, Bactris gasipaes, Benincasa hispida, Celastrus paniculatus, Cetraria islandica, Chenopodium quinoa, Cinchona succirubra, Citrus bergamia, Citrus sinensis, Coriandrum sativum, Codium tomentosum, Commiphora molmol, Crataegus cuneata, Cucumis sativus, Eucalyptus globulus, Gleditsia sinensis, Gnetum amazonicum, Hibiscus rosa-sinensis, Jasminum officinale, Lonicera caprifolium, Lonicera japonica, Lycopersicon esculentum, Malus pumila, Matricaria recutita, Maximiliana maripa, Melaleuca hypericifolia, Melaphis chinensis, Mentha piperita, Mouriri apiranga, Nasturtium officinale, Nelumbo nucifera, Oenothera biennis, Ophiopogon japonicus, Persea americana, Paffia paniculata, Phellodendron amurense, Phyllanthus emblica, Pisum sativum, Potentilla erecta, Pterocarpus santalinus, Rehmannia chinensis, Reseda luteola, Ribes nigrum, Rosa centifolia, Rubus thunbergii, Spondias amara, Styrax benzoin*, and *Thymus vulgaris*.

Extract sources also include algae. Families of algae used as extract sources include Acrochaeticaceae, Characeae, Codiaceae, Fucaceae, Laminariaceae, Lemaneaceae, Ulvaceae, and Pamariaceae. Preferred algae species include *Lemanea fluviatilis* (red algea), (L.), *Ascophyllum nodosum* (brown alga), *Lemanea fluviatilis, Lemanea fucina* (red algea), *Ulva lactuca* (green alga), *Laminaria digitata, Laminaria ochroleuca*.

Extract sources also include members of the kingdom of Fungi. For extraction classes of Homobasidiomycetes (or true mushrooms) can be used. Some exemplary mushrooms families include: Meripilaceae, Tricholomataceae, and Ganodermataceae (maitake, shiitake, reishi mushrooms). Specific species include: *Agaricus bisporus, Agaricus campestris, Flammulina velutipes Hypsizygus tessulatus, Lentinus edodes, Phellinus linteus, Pleurotus cornucopiae, Pleurotus ostreatus, Tremella fuciformis, Sparassis crispa, Tuber magnatum*, and *Volvariella volvacea*.

Species from the division of Bryophyta, Kingdom of plantae (which includes mosses) can be used as extract sources, and some species of lichen can also be used for extraction.

Marine sources, such as plants, algae, plankton, and fish, are used to produce extracts. Protein and lipid extract sources include plant, animal, fish and human (eg. Placenta) materials. Milk can be used as an extract source to isolate and concentrate proteins, peptides, and lipids.

All of the compositions and methods disclosed and claimed herein can be made and executed without undue experimentation in light of the present disclosure. While the compositions and methods of the present disclosure have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope, and concept of the invention as defined by the appended claims.

Personal Care Compositions

The personal care compositions of the present invention include any composition that may be applied to the skin, hair, eyelashes, eyebrows, lips, or nails to provide a cosmetic or beneficial effect. These personal care compositions include, but are not limited to, skin care compositions, skin cleansing compositions, make-up, facial lotions, cream moisturizers, body washes, body lotions, foot creams, hand creams, lipstick, eyeshadow, foundation, facial powders, deodorant, shaving cream compositions, nail polishes, shaving lotions, cream depilatories, lotion depilatories, facial masks made with clay materials, anti-aging products, shampoos, hair conditioners, hair treatment creams, styling gels, styling foams, hair mousses, hair sprays, set lotions, blow-styling lotions, hair color lotions, and hair relaxing compositions.

In cosmetic compositions, biologically-derived 1,3-propanediol is present in amounts up to about 50% by weight based on the weight of the total composition, preferable up to about 35% by weight, and more preferable up to about 10% by weight of the total composition.

In other personal care compositions, biologically-derived 1,3-propanediol is present in amounts up to about 12% by weight based on the weight of the total composition, though some compositions, for example hair gels and deodorants, can contain up to about 30% by weight or 40% by weight, respectively, biologically-derived 1,3-propanediol based on the weight of the total composition.

The personal care compositions of the present invention also may one or more conventional cosmetic or dermatological additives or adjuvants, including, but not limited to, fillers, surfactants, thixotropic agents, antioxidants, preserving agents, dyes, pigments, fragrances, thickeners, vitamins, hormones, moisturizers, UV absorbing organic sunscreens, UV scattering inorganic sunscreens, wetting agents, cationic, anionic, nonionic or amphoteric polymers, and hair coloring active substances. These adjuvants are well known in the field of cosmetics and are described in many publications, for example see Harry's Cosmeticology, 8th edition, Martin Rieger, ed., Chemical Publishing, New York (2000).

Among these adjuvants, the fillers are generally present in personal care products in a maximum proportion of about 99.9% by weight relative to the total weight of the composition. These fillers, in the form of very fine powders, can be of natural or synthetic origin and include, but are not limited to, mineral powders, such as talc, kaolin, mica, silica, silicates, alumina, zeolites, hydroxyapatite, sericite, titanium dioxide, titanium micas, barium sulfate, calcium carbonate, calcium sulfate, bismuth oxychloride, boron nitride and metal powders such as aluminum powder; plant powder, such as corn starch, wheat starch or rice starch powders; organic powders, such as polyamide powder, polyester powder, polytetrafluoroethylene powder, the powder of fluorinated alkanes, polyethylene powder and other inert plastics. These various powders can also be coated, for example with metal salts of fatty acids, amino acids, lecithin, collagen, silicone corn pounds, fluoro compounds or with any common coating agent.

The personal care compositions of this invention may also contain surfactants or wetting agents, preferably at about 0.001 to about 18%, more preferably at about 0.005 to about 15% by weight of the total composition. The terms "surfactants" and "wetting agents" as used herein refer to surface-active agents which, when added to water, cause it to penetrate more easily into, or spread on the surface of another material, by reducing the surface tension of the water at the water-air or water-oil interface. By "surface active agent" is meant any compound that reduces surface tension when dissolved in water or water solutions. The selection of a surfactant for this purpose presents a wide range of possibilities known in the art. Suitable surfactants include, but are not limited to, the following:

(1) anionic surfactants, such as metallic or alkanolamine salts of fatty acids for example sodium laurate and triethanolamine oleate; alkyl benzene sulfones, for example triethanolamine dodecyl benzene sulfonate; alkyl sulfates, for example sodium lauryl sulfate; alkyl ether sulfates, for example sodium lauryl ether sulfate (2 to 8 EO); sulfosuccinates, for example sodium dioctyl sulfonsuccinate; monoglyceride sulfates, for example sodium glyceryl monostearate monosulfate; isothionates, for example sodium isothionate; methyl taurides, for example Igepon T; acylsarcosinates, for example sodium myristyl sarcosinate; acyl peptides, for example Maypons and lamepons; acyl lactylates, polyalkoxylated ether glycollates, for example trideceth-7 carboxylic acid; phosphates, for example sodium dilauryl phosphate.

(2) cationic surfactants, such as amine salts, for example sapamin hydrochloride; quatenary ammonium salts, for example Quaternium 5, Quaternium 31 and Quaternium 18;

(3) amphoteric surfactants, such as imidazol compounds, for example Miranol; N-alkyl amino acids, such as sodium cocaminopropionate and asparagine derivatives; betaines, for example cocamidopropylebetaine;

(4) nonionic surfactants, such as fatty acid alkanolamides, for example oleic ethanolamide; esters or polyalcohols, for example Span; polyglycerol esters, for example that esterified with C12-18 fatty acids and one or several OH groups; polyalkoxylated derivatives, for example polyoxy:polyoxyethylene stearate (available for example from McIntyre Co.); ethers, for example polyoxyethe lauryl ether (available for example from Stepan Co., Northfield, Ill., as Stepanol® ES); ester ethers, for example Tween®; amine oxides, for example coconut and dodecyl dimethyl amine oxides. Mixtures of two or more of the above surfactants can be employed in the compositions according to the invention.

The personal care compositions of this invention may also contain thixotropic or gelling agents, preferably at about 0.02 to about 20%, more preferably at about 0.05 to about 18% by weight of the total composition. Suitable thixotropic or gelling agents include, but are not limited to, stearates of aluminum, calcium, magnesium, potassium, sodium, or zinc; hydroxystearate, isostearate, laurate, linoleate, myristate, oleate, olivate, palmate, palmitate, tallowate, rosinate, and the like, and fatty acid esters of glycol, triglycerides, mixtures of fatty alcohols, cholesterol derivatives and in particular hydroxycholesterol, and clay minerals which swell in the presence of oil, and in particular those belonging to the montmorillonite group.

The personal care compositions of this invention may also contain antioxidants, preferably at about 0.001 to about 10%, more preferably at about 0.01 to about 8% by weight of the total composition. Suitable antioxidants are ingredients, which assist in preventing or retarding spoilage. Examples of antioxidants suitable for use in the compositions of the invention include, but are not limited to, potassium sulfite, sodium bisulfite, sodium erythrobate, sodium metabisulfite, sodium sulfite, propyl gallate, cysteine hydrochloride, butylated hydroxytoluene, butylated hydroxyanisole, and the like.

The personal care compositions of this invention may also contain preserving agents, preferably at about 0.001 to about 8%, more preferably at about 0.01 to about 5% by weight of the total composition. Suitable preserving agents include, but are not limited to, benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, ethyl paraben, propyl paraben, diazolidinyl urea, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, Phenonip®, Kathon® and all of those disclosed on pages 570 to 571 of the Cosmetic, Toiletry and Fragrance Association (CTFA) Cosmetic Ingredient Handbook, Second Edition, 1992, which is herein incorporated by reference.

The personal care compositions of this invention may also contain dyes, preferably at about 0.1 to about 15%, by weight of the total composition. Suitable dyes include, but are not limited to, eosin derivatives such as D&C Red No. 21 and halogenated fluorescein derivatives such as D&C Red No. 27, D&C Red Orange No. 5 in combination with D&C Red No. 21 and D&C Orange No. 10.

The personal care compositions of this invention may also contain pigments, preferably at about 0.1 to about 15% by weight of the total composition. Suitable pigments may be inorganic or organic or alternatively metal lakes and include, but are not limited to, titanium dioxide, zinc oxide, barium oxide, D&C Red No. 36 and D&C Orange No. 17, the calcium lakes of D&C Red Nos. 7, 11, 31 and 34, the barium lake of D&C Red No. 12, the strontium lake D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, ultramarine blue, and carbon black particles.

The personal care compositions of this invention may also contain fragrances, preferably at about 0.01 to about 10%, by weight of the total composition. Numerous fragrances, both natural and synthetic, are well known in the art. For example, Secondini (Handbook of Perfumes and Flavors, Chemical Publishing Co., Inc., New York, 1990), incorporated herein by reference, describes many of the natural and synthetic fragrances used in cosmetics. Suitable natural fragrances include, but are not limited, to jasmines, narcissus, rose, violet, lavender, mint, spice, vanilla, anise, amber, orange, pine, lemon, wintergreen, rosemary, basil, and spruce. Suitable synthetic fragrances include, but are no limited to, acetaldehyde, C7 to C16 alcohols, benzyl acetate, butyric acid, citric acid, isobutyl phenyl acetate, linalyl butyrate, malic acid, menthol, phenyl ethyl cinnamate, phenyl propyl formate, tannic acid, terpineol, vanillin, amyl salicylate, benzaldehyde, diphenyl ketone, indole, and the like.

The personal care compositions of this invention may also contain thickeners, preferably at about 0.001 to about 25%, more preferably at about 0.1 to about 15%, by weight of the total composition. Suitable thickeners include, but are not limited to, starch; gums, such as gum arabic or xanthan gum; carbomer polymers, such as Carbopol® 941, 940, 934 (available from Union Carbide Co., Midland, Mich.), and Ultrez 10; kaolin or other clays, ethylene glycol monostearate, carboxyvinyl polymer, acrylic copolymers, hydroxyethyl cellulose, and hydroxypropyl cellulose.

The personal care compositions of this invention may also contain vitamins and/or coenzymes, preferably at about 0.001 to about 10%, more preferably at about 0.01% to about 8%, most preferably at about 0.05% to about 5% by weight of the total composition. Suitable vitamins include, but are not limited to, ascorbic acid and derivatives thereof; the B vitamins, such as thiamine, riboflavin, pyridoxin, and the like; vitamin A and derivatives thereof; vitamin E and derivatives thereof; vitamin D and vitamin K; as well as coenzymes such as thiamine pyrophosphate, flavin adenine dinucleotide, folic acid, pyridoxal phosphate, tetrahydrofolic acid, and the like.

The personal care compositions of this invention may also contain hormones, preferably at about 0.0001 to about 0.01% by weight of the total composition. Suitable hormones include, but are not limited to, estrogen, progesterone, pregnenolone, testosterone, estradiol, hydrocortisone, and cortisone.

The personal care compositions of this invention may also contain moisturizers, preferably at about 0.1 to about 30%, more preferably at about 0.5 to about 25%, most preferably at about 1 to about 20% by weight of the total composition. These moisturizers include water-soluble, low molecular weight moisturizers, fat-soluble, low molecular weight moisturizers, water-soluble, high molecular weight moisturizers and fat-soluble, high molecular weight moisturizers. Suitable water-soluble, low molecular weight moisturizers include, but are not limited to, serine, glutamine, sorbitol, mannitol, pyrrolidone-sodium carboxylate, glycerin, propylene glycol, 1,3-butylene glycol, ethylene glycol, polyethylene glycol (polymerization degree n=2 or more), polypropylene glycol (polymerization degree n=2 or more), polyglycerin (polymerization degree n=2 or more), lactic acid and lactate. The water soluble, low molecular weight moisturizer can also be biologically-derived 1,3-propanediol. Suitable fat-soluble, low molecular weight moisturizers include, but are not limited to, cholesterol and cholesterol ester. Suitable water-soluble, high molecular weight moisturizers include, but are not limited to, carboxyvinyl polymers, polyaspartate, tragacanth, xanthane gum, methyl cellulose, hydroxymethyl cellulose, hydroxyethyl cellulose, hydroxypropyl cellulose, carboxymethyl cellulose, water-soluble chitin, chitosan and dextrin. Suitable fat-soluble, high molecular weight moisturizers include, but are not limited to, polyvinylpyrrolidone-eicosene copolymers, polyvinylpyrrolidone-hexadecene copolymers, nitrocellulose, dextrin fatty acid ester and high molecular silicone.

The personal care compositions of this invention may also contain UV absorbing organic sunscreens, preferably at about 0.001 to about 20%, more preferably at about 0.01 to about 10%, most preferably at about 0.05 to about 8% by weight of the total composition. UV absorbing organic sunscreens are herein defined as organic chemicals that absorb ultraviolet light of wavelengths between 290 and 329 nm. Suitable UV absorbing organic sunscreens include, but are not limited to, para-aminobenzoic acid, ethyl para-aminobenzoate, amyl para-aminobenzoate, octyl para-aminobenzoate, ethylene glycol salicylate, phenyl salicylate, octyl salicylate, benzyl salicylate, butylphenyl salicylate, homomethyl salicylate, benzyl cinnamate, 2-ethoxyethyl para-methoxycinnamate (such as Parsol® available from Givaudan-Roure Co.), octyl para-methoxycinnamate, glyceryl mono(2-ethylhexanoate) dipara-methoxycinnamate, isopropyl para-methoxycinnamate, diisopropyl-diisopropylcinnamic acid ester mixtures, urocanic acid, ethyl urocanate, hydroxymethoxybenzophenone, hydroxymethoxybenzophenonesulfonic acid and salts thereof, dihydroxymethoxybenzophenone, sodium dihydroxymethoxybenzophenonedisulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, and 2-(2-hydroxy-5-methylphenyl)benzotriazole. UV scattering inorganic sunscreen materials, such as inorganic pigments and metal oxides, including but not limited to oxides of titanium (such as SunSmart available from Cognis Corp), zinc, and iron, may also be incorporated into the compositions of the instant invention. UV scattering inorganic sunscreens are herein defined as inorganic substances that scatter ultraviolet light of wavelengths between 210 and 280 nm. These UV scattering inorganic sunscreens may be used in the personal care compositions of this invention at concentrations of preferably about 0.001 to about 40%, more preferably at about 0.01 to about 10%, most preferably at about 0.05 to about 8% by weight of the total composition.

The personal care compositions of this invention may also contain other film-forming polymers, preferably at about 0.01 to about 20%, more preferably at about 0.01% to about 10%, by weight of the total composition. These polymers serve as conditioners to coat the skin or hair, or to coat particles that are present in the composition. These polymers may be cationic, anionic, nonionic, or amphoteric. Cationic polymers are herein defined as synthetic or natural polymers that contain, or have been modified to contain, positively charged groups and/or groups that can ionize to positively charged groups. Suitable cationic polymers, include, but are not limited to, cationized cellulose, cationized guar gum, diallyly quaternary ammonium salt/acrylamide copolymers, quaternized polyvinylpyrrolidone and derivatives thereof, polyquaternium-1, polyquaternium-2, polyquaternium-5, polyquaternium-6, polyquaternium-7, polyquaternium-8, polyquaternium-9, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-27, polyquaternium-28, polyquaternium-29, polyquaternium-30, and mixtures thereof, wherein the compound designation is the name adopted for the compound by the CTFA, and found in the CTFA International Cosmetic Ingredient Dictionary, J. Nikitakis, ed., Cosmetic, Toiletry and Fragrance Association, Inc., Washington, D.C. (1991), incorporated herein by reference.

Anionic polymers are herein defined as synthetic or natural polymers that contain, or have been modified to contain, negatively charged groups and/or groups that can ionize to negatively charged groups. Suitable anionic polymers, include, but are not limited to, polyacrylic acid, polymethacrylic acid, carboxymethylcellulose, hydroxymethylcellulose, and starch.

Nonionic polymers are herein defined as synthetic or natural polymers that do not contain any charged groups. Suitable nonionic polymers, include, but are not limited to, polyvinylpyrrolidone, polyvinyl alcohol, polyethylene glycol, polyvinylacetate, polysiloxanes, and copolymers of vinylpyrrolidone and vinyl acetate.

Amphoteric polymers are herein defined as synthetic or natural polymers that contain both negatively and positively charged groups and/or groups that can ionize to give positively and negatively charged groups. Suitable amphoteric polymers are described by Marchi et al. in U.S. Pat. No. 5,643,672, incorporated herein by reference. Examples include, but are not limited to, polymers resulting from the copolymerization of a monomer derived from a vinyl compound carrying a carboxyl group, such as acrylic acid, methacrylic acid, maleic acid and alpha-chloroacrylic acid, and a basic monomer derived from a substituted vinyl compound containing at least one basic nitrogen atom, such as dialkylaminoalkyl(meth)acrylates and dialkylaminoalkyl(meth)acrylamides, products sold by the company National Starch under the name Amphomer®, methyl methacrylate/ethyldimethylcarboxymethylammonium methacrylate copolymers, such as the products sold by Chimex under the name Mexomer PX (CTFA name: "polyquaternium-30"), methacryloylethylbetaine/methacrylate copolymer sold by Sandoz under the name Diaformer, the methacryloylethylbetaine/methacrylate copolymer sold by Amerchol under the name Amersette, polysiloxane polyorganobetaine copolymers sold by Goldschmidt under the name Abil® B 9950 (CTFA Name: "Dimethicone PropylPG-Betaine"), the polydimethylsiloxane containing alkylphosphobetaine groups sold by Siltech under the name Pecosil® SPB-1240, and the oxyethyleneoxypropylene organobetaine/siloxane copolymer sold by Goldschmidt under the name BC 1610.

According to one embodiment of the present invention, the compositions are anhydrous and comprise a fatty phase in a proportion generally of from about 10 to about 90% by weight relative to the total weight of the composition, wherein the fatty phase contains at least one liquid, solid or semi-solid fatty substance. The fatty substances include, but are not limited to oils, fats, waxes, gums, and so-called pasty fatty substances. The oils in the fatty phase may be of mineral, animal, plant or synthetic origin, and may or may not be volatile at room temperature.

Oils of mineral origin include, but are not limited to, liquid paraffin and liquid petroleum jelly. Oils of animal origin include, but are not limited to, squalene and squalane. Oils of plant origin include, but are not limited to, sweet aim and oil, beauty-leaf oil, palm oil, avocado oil, jojoba oil, sesame oil, olive oil, castor oil and cereal germ oils such as, for example, wheatgerm oil. Synthetic oils include, but are not limited to:

(1) esters of the following formula: R1-COOR2 in which: R1 represents a higher fatty acid residue containing from 7 to 20 carbon atoms, and R2 represents a hydrocarbon-based radical containing from 3 to 30 carbon atoms. These esters, include, but are not limited to: purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate and esters derived from lanolic acid, such as isopropyl lanolate and isocetyl lanolate. Other synthetic oils include, but are not limited to, isododecane (available for example from Exxon-Mobil Chemical Co., Houston, Tex., under the trade name of Isopar®), isohexadecane, polyisobutenes and hydrogenated polyisobutene, as well as acetylglycerides, octanoates and decanoates of polyalcohols such as those of glycol and of glycerol, ricinoleates of alcohols or of polyalcohols, such as cetyl ricinoleate, propylene glycol dicaprylate and diisopropyl adipate;

(2) fatty alcohols including, but not limited to, oleyl alcohol, linoleyl alcohol, linolenyl alcohol, isostearyl alcohol and octyldodecanol;

(3) ethoxylated oils and fats, including but not limited to, triglycerides with a polyethylene glycol chain inserted, ethoxylated mono- and di-glycerides, polyethoxylated lanolins, ethoxylated butter derivatives, polyethylene glycol derivatives of glyceryl cocoate, glyceryl caprate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, glyceryl tallowate, glyceryl cocoate, and polyethylene glycol based polyethoxylated fatty alcohols such as PEG 40 hydrogenated castor oil (commercially available under the tradename Cremophor® from BASF), PEG 7 glyceryl cocoate and PEG 20 glyceryl laurate (commercially available from Henkel under the tradenames Cetiol® HE and Lamacit® GML 20 respectively), and polyethylene glycol ethers of ceteryl alcohol such as Ceteareth 25 (available from BASF under the trade name Cremophor® A25).

(4) silicone oils including, but not limited to, optionally functionalized linear polydiorganosiloxanes, cyclic polydiorganosiloxanes and in particular cyclotetra- and cyclopentadimethicones and organopolysiloxanes such as alkyl, alkoxy or phenyl dimethicones, and in particular phenyltrimethicone (available from Dow Corning, Midland, Mich., as Simethicone and DC 200 Fluids);

(5) fluoro oils including, but not limited to, fluoroalkanes and fluoropolyethers, partially fluorinated hydrocarbon-based oils, and fluoropolymers represented by the monomer unit: X1X2C=CX3F wherein X1, X2, and X3 are independently H or F.

The waxes in the fatty phase may be of mineral, fossil, animal, plant or synthetic origin or alternatively can be hydrogenated oils or fatty esters, which are solid at 25° C. The mineral waxes, include, but are not limited to, microcrystalline waxes, paraffin, petroleum jelly and ceresine. The fossil waxes, include, but are not limited to, ozocerite and montan wax. The waxes of animal origin, include, but are not limited to beeswax, spermaceti, lanolin wax and derivatives obtained from lanolin such as lanolin alcohols, hydrogenated lanolin, hydroxylated lanolin, acetylated lanolin, lanolin fatty acids and acetylated lanolin alcohol. The waxes of plant origin, include, but are not limited to, candelilla wax, carnauba wax, Japan wax and cocoa butter. The synthetic waxes, include, but are not limited to, ethylene homopolymers, seracite, shea butter, and copolymers of ethylene and of a monomer corresponding to the formula: CH2=CH—R3 in which: R3 represents an alkyl radical containing from 1 to 30 carbon atoms or an aryl or aralkyl radical. The alkyl radical of 1 to 30 carbon atoms is preferably a methyl, ethyl, propyl, isopropyl, butyl, decyl, dodecyl or octadecyl radical. Waxes obtained by Fisher-Tropsch synthesis and silicone waxes may also be used.

The hydrogenated oils, which are solid at 25° C., include, but are not limited to, hydrogenated castor oil, hydrogenated palm oil, hydrogenated tallow and hydrogenated coconut oil. The fatty esters, which are solid at 25° C., include, but are not limited to, propylene glycol monomyristate and myristyl myristate. Waxes which can be used in the compositions according to the invention include, but are not limited to, cetyl alcohol, stearyl alcohol, mono-, di- and triglycerides which are solid at 25° C., stearic monoethanolamide, colophony and its derivatives such as glycol abietate and glyceryl abietate, sucroglycerides and calcium, magnesium, zinc and aluminum oleates, myristates, lanolates, stearates and dihydroxystearates.

The pasty-type fatty substances can be of mineral, animal, plant or synthetic origin. The pasty fatty substances include, but are not limited to, synthetic esters such as arachidyl propionate, polyvinyl laurate, polyethylene waxes and organopolysiloxanes such as alkyldimethicones, alkoxydimethicones or dimethicone esters.

These anhydrous compositions can be in various forms including, but not limited to, an oily gel, solid products, such as compacted or cast powders, or alternatively sticks such as, for example lipsticks. When the compositions according to the present invention are in the form of an oily gel, they generally contain a thixotropic or gelling agent, examples of which are given supra. The thixotropic agents can be present in various proportions depending on the desired texture of the compositions. However, in most cases, they are present in a proportion of from about 1 to about 20% by weight relative to the total weight of the composition.

The anhydrous compositions of the present invention may be used in particular as skin care, skin cleansing, or make-up products. When they are present in the form of make-up products, they can be foundations, mascaras, eyeliners, lipsticks, eyeshadows or blushers. These compositions are generally colored and contain dyes and/or pigments as cosmetic adjuvants, which are described supra.

According to a another embodiment of the present invention, the compositions can be used to form stable dispersions in the form of a water-in-oil (W/O) or oil-in-water (O/W) emulsion, which comprise: a fatty phase, as described supra, in a proportion of from about 0.1 to about 50% by weight relative to the total weight of the emulsion; an aqueous phase in a proportion of from about 50 to about 98.9% by weight relative to the total weight of the emulsion, said aqueous phase containing biologically-derived 1,3-propanediol, in a proportion of from about 1% to about 5% by weight relative to the total weight of the emulsion; and at least one emulsifier in a proportion of from about 1 to about 10% by weight relative to the total weight of the emulsion. Suitable emulsifiers are well known in the field of cosmetic products. For example, water-in-oil emulsifiers include, but are not limited to, sterols such as cholesterol and its associated esters and alcohols, lanolin, calcium oleate and other fatty acid soaps of divalent metals, beeswax, and polyhydric alcoholics of fatty acids such as glyceryl monostearate and sorbitan sesquioleate. Suitable oil-in-water emulsifiers include, but are not limited to, ordinary soaps, partially sulfated fatty alcohols, Cetomacrogol B.P., polyethoxylated esters known as Spans, cetydimethylbenzyl ammonium chloride, and gums and gum substitutes These emulsions, which are in the form of creams, have good film-forming properties and give a very satisfactory sensation after they have been applied. Such emulsions can be used as skin care, skin cleansing, or make-up products. When these compositions are skin care products, they can be anti-wrinkle products for improving the appearance of the skin. When these compositions are make-up products, they may be foundations or mascaras, containing a certain proportion of the pigments and/or dyes described supra.

In another embodiment of the present invention, the personal care compositions are hair care compositions. Hair care compositions are herein defined as compositions for the treatment of hair, including but not limited to shampoos, conditioners, hair treatment creams, aerosols, gels, hair sprays, set lotions, blow styling lotions, hair relaxing compositions, and mousses. The hair care compositions of the present invention comprise an effective amount of biologically-derived 1,3-propanediol in a cosmetically acceptable medium. An effective amount of biologically-derived 1,3-propanediol for use in a hair care composition is herein defined as a proportion of from about 1% to about 30% by weight relative to the total weight of the composition. Components of a cosmetically acceptable medium for hair care compositions are described by Omura et al. in U.S. Pat. No. 6,139,851 and Cannell et al. in U.S. Pat. No. 6,013,250, both of which are incorporated herein by reference. For example, these hair care compositions can be aqueous, alcoholic or aqueous-alcoholic solutions, the alcohol preferably being a monohydric alcohol such as ethanol or isopropanol, in a proportion of from about 1 to about 75% by weight relative to the total weight for the aqueous-alcoholic solutions. The hair care compositions may also contain other polyhydric alcohols including, but not limited to, ethylene glycol, propylene glycol, 1,3-butylene glycol, glycerine, sorbitol, 2-methyl-1,3-propanediol, and polyethylene glycol. Additionally, the hair care compositions may contain one or more conventional cosmetic or dermatological additives or adjuvants, as described supra.

The viscosity of the various personal care compositions depends on the nature of the composition. For example, emulsions typically have a viscosity up to about 250,000 cps. Other cosmetic compositions have viscosity up to about 600,000, cps, but preferably up to 300,000 cps and more preferable, up to 250,000 cps. Water thin compositions, for example sprays or some conditioners, have a viscosity of less than about 100 cps.

The present invention also comprises a method for forming a protective film on skin or hair by applying one of the compositions described above comprising biologically-derived 1,3-propanediol to the skin or hair and allowing the formation of the protective film. The compositions of the present invention may be applied to the skin or hair by various means, including, but not limited to, spraying, brushing, and applying by hand. The composition is left in contact with the skin or hair for a period of time sufficient to form the protective film, preferably for at least about 0.1 to 60 min.

Though the presently disclosed personal care compositions typically have human application, personal care compositions for other animals, particularly mammals, more particularly canine, feline, or equine, are also within the scope of the present disclosure.

Uses of esters from bio-derived 1,3-propanediol in personal care products

The monoesters and diesters of bio-derived 1,3-propanediol are useful in a variety of applications.

Esters as described herein are suitable, in a non-limiting way, for use in the composition of liquid hand soaps, shampoos and liquid detergents as emulisifers, pearlizing agents, surfactants, gelling agents, structurants, thickeners, or opacifiers. The esters containing about 1 to about 24 carbons in the alkyl chain are particularly useful in liquid soap, shampoo and detergent applications.

The esters of the present invention are also useful as an active ingredient in cosmetics as emollients. In other cosmetic applications such esters are useful in the deliver, application or effectiveness of the cosmetic. In this use the esters act as an additive or adjuvant. Specifically, in a non-limiting way, such esters can be uses as a humectant, opacifier, pearlizing agent, gelling agent, emulsifier, surfactant, structurant, thickener, compatibilizer or solvent for cosmetics and personal care products. The fatty acid esters of the present invention, containing about 8 to about 24 carbons in the alkyl chain are particularly useful in cosmetic applications.

Such esters are also useful as a solvent for botanical products. Such botanical products include, but are not limited to, all plants, their seeds, stems, roots, flowers, leaves, pollen, spices and oils.

Esters as described herein can also be used in inks as an emulsifier in cosmetic inks like tattoos or henna dyes.

Such esters are useful in preparation of solid or near solid personal care products such as stick deodorants and bronzing sticks.

The esters of the present invention are also useful in personal care compositions as an emulsifier, humectant, gelling agent, surfactant, structurant, thickener, compatibilizer or solvent.

Such personal care applications can be directs to any animal, especially avians, reptiles and mammals. The preferred applications are directed to humans, canine, feline and equine species. The most preferred applications are directed to human species.

Detergent Compositions

As mentioned above, 1,3-propanediol can be incorporated into numerous compositions as a glycol component. For example, 1,3-propanediol can be part of or the sole glycol component of detergent compositions.

In liquid detergent compositions, the glycol component typically is an emulsifier and/or phase stabilizer or a solvent. Exemplary liquid detergents include, but are not limited to, hand or machine dish washing detergent, laundry detergent, clothing softener, and car wash detergent. Glycols are present in the aforementioned detergent compositions in amounts well known to those of ordinary skill in the appropriate art, typically up to about 20% by weight based on the weight of the total composition. A typical formulation may include, but is not limited to, the following components by weight percent: 0.0-20.0% glycol, 5.0-40.0% fatty acid ester, and 1.0 to 50.0% surfactant or surfactant blend. Additionally, up to 5.0% by weight of the following components may be included: suds stabilizer, pH buffer, and enzymes.

Detergent Compositions Comprising 1,3-propanediol Esters

Esters as describe herein are also suitable, in a non-limiting way, for use in the composition of liquid soaps and liquid detergents as emulisifers, pearlizing agents, surfactants, gelling agents, structurant, thickener, or opacifier. The esters containing about 1 to about 24 carbons in the alkyl chain are particularly useful in liquid detergent applications.

Such liquid soaps and liquid detergents can be directs to any animal, especially avians, reptiles and mammals. The preferred applications are directed to humans, canine, feline and equine species. The most preferred applications are directed to human species.

In addition, the esters of the instant application may used for powder detergents, such as powder dishwasher detergent, and textiles detergents.

Such esters are also useful as a solvent for botanical products in detergents. Such detergent compositions comprising botanical products include botanicals directed to plants, their seeds, stems, roots, flowers, leaves, pollen, spices and oils.

The esters in the detergent compositions described herein may also function as an antimicrobial agent.

A further description of types of detergent formulations comprising fatty acid esters can be found in "Liquid Detergents" (Surfactant Science Series Volume 129, Taylor & Francis Group, Boca Raton, Fla., 2005). Additional description follows, including reference to light-duty and heavy-duty detergents, both of which are the subject of the detergents compositions provided herein.

Light-duty liquid detergents are for dishwashing (by hand) and liquid detergents for textile, delicate garments—usually the exposure times are relatively short, about 20 minutes and the use concentrations are low, about 0.15%. Esters in these compositions provide benefit as non-ionic surfactants.

Heavy-duty liquid detergents (HDLD) are for textile applications (for washing machines). In this context the fatty acid esters are mostly the non-ionic surfactants. The non-ionic surfactants (beside the anionic surfactants) are primarily responsible for wetting the surfaces of fabrics as well as the soil (reducing surface and interfacial tension), helping to lift the stains off the fabric surface, and stabilizing dirt particles and/or emulsifying grease droplets. Esters in these compositions provide additional benefits as aesthetic ingredients and help to create a microemulsion.

TABLE 1

General formulation of a Structured HDLD:

| Ingredient | Function | % |
|---|---|---|
| Sodium Linear Alkylbenzene Sulfonate | Anionic surfactant | 0-30 |
| Sodium Alkyl Ether Sulfate | Anionic surfactant | 0-10 |
| Alcohol Ethoxylate | Nonionic surfactant | 0-10 |
| Sodium Carbonate | Builder | 0-25 |
| Zeolite | Builder | 0-25 |
| Sodium Perborate | Bleach | 0.0-10.0 |
| Polymer | Stabilizer | 0.0-1.0 |
| Protease | Enzyme | 0.0-1.5 |
| Fluorescent Whitening Agent | Brightener | 0.0-0.5 |
| Boric Acid | | 0.0-5.0 |
| Preservative | | 0.05-0.2 |
| Fragrance | | 0.0-0.6 |
| Colorant | | 0.00-0.2 |

TABLE 2

General formulation of an Unstructured HDLD:

| Ingredient | Function | % |
|---|---|---|
| Sodium Linear Alkylbenzene Sulfonate | Anionic surfactant | 0-15 |
| Sodioum Alkyl Ether Sulfate | Anionic surfactant | 0-15 |
| Alcohol Ethoxylate | Nonionic surfactant | 0-15 |
| Sodium Citrate | Builder | 0-10 |
| Monoethanolamine | Buffer | 0-5 |
| Soap | Defoamer | 0-5 |
| Protease | Enzyme | 0-1.5 |
| Fluorescent Whitening Agent | Brightener | 0-0.5 |
| Boric Acid | Enzyme stabilizer | 0-5.0 |
| Ethanol | Solvent | 0.0-5 |
| Sodium Xylene Sulfonate | Hydrotrope | 0-10.0 |
| Preservative | | 0.05-0.2 |
| Fragrance | | 0-0.6 |
| Colorant | | 0-0.2 |

The fatty acid esters of the instant invention may also function as non-ionic cosofteners. Generally glycol fatty acid esters deliver good softness and static control without any drawback.

Other type of detergents within the instant invention include cream cleaners, as it has been found that fatty acid esters provide for microemulsion characteristics that benefit cream cleaners or detergents. Gel cleaners maybe formulated within the instant invention for the same reasons.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

All ingredients used in the preparation of the personal care compositions described in the following Examples are available commercially unless otherwise noted.

The meaning of abbreviations used is as follows "% wt." means percent by weight; "qs" means as much as suffices; "EDTA" means ethylenediamine tetraacetate; "° C." means degrees Centigrade; "° F." is degrees Fahrenheit, "Bio-PDO" means biologically-derived 1,3-propanediol; "ppm" is parts per million; "AU" is absorbance unit; "nm" is nanometer(s); "GC" is gas chromatograph; "APHA" is American Public Health Association; "cps" is centipoise; "f/t" is freeze/thaw; "mPa·s" is milliPascal seconds; "D.I." is deionized.

General Methods:

Standard recombinant DNA and molecular cloning techniques used in the Examples are well known in the art and are described by Sambrook, J., Fritsch, E. F. and Maniatis, T., *Molecular Cloning: A Laboratory Manual*, Cold Spring Harbor Laboratory Press, Cold Spring Harbor, N.Y., 1989, by T. J. Silhavy, M. L. Bennan, and L. W. Enquist, *Experiments with Gene Fusions*, Cold Spring Harbor Laboratory, Cold Spring Harbor, N.Y., 1984, and by Ausubel, F. M. et al., *Current Protocols in Molecular Biology*, Greene Publishing Assoc. and Wiley-Interscience, N.Y., 1987.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or by Thomas D. Brock in *Biotechnology: A Textbook of Industrial Microbiology*, Second Edition, Sinauer Associates, Inc., Sunderland, Mass., 1989.

All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.), unless otherwise specified.

Glycerol used in the production of 1,3-propanediol was obtained from J. T. Baker Glycerin USP grade, Lot 325608 and G19657.

Differential Scanning calorimetry: DSC thermograms were recorded using Universal V3 1A TA instrument under constant stream of nitrogen with a heating and cooling rate of 10° C./min.

NMR: 1H NMR spectra were recorded on Bruker DRX 500 using XWINNMR version 3.5 software. Data was acquired using a 90 degree pulse (p1) and a 30 second recycle delay (d1). Samples were dissolved in deuterated chloroform and nondeuterated chloroform was used as internal standard.

Isolation and Identification Bio-PDO

The conversion of glycerol to bio-PDO was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 NH2SO4 as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of bio-PDO was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Production of Bio-Based Monoesters and Diesters from Bio-Produced 1,3-propanediol.

Monoesters and diester of bio-produced 1,3-propandiol may be produced by combining bioPDO with organic acid. The combination is to be preformed in dry conditions under heat and prolong agitation with a selected catalyst. The ratio of monoester to diester produced will vary according to the molar ratio of acid to bioPDO and the selection of catalyst.

The production of esters was confirmed using $^1$H nuclear magnetic resonance. Analyses were performed using standard techniques and materials available to one of skill in the art of $^1$H NMR.

Proton Nuclear Magnetic Resonance ($^1$H NMR) Spectroscopy is a powerful method used in the determination of the structure of unknown organic compounds. It provides information concerning: the number of different types of hydrogens present in the molecule, the electronic environment of the different types of hydrogens and the number of hydrogen "neighbor" a hydrogen has.

The hydrogens bound to carbons attached to electron withdrawing groups tend to resonate at higher frequencies from TMS, tetramethylsilane, a common NMR standard. The position of where a particular hydrogen atom resonates relative to TMS is called its chemical shift ($\delta$). Typical chemicals shifts of fatty ester are as follows.

$\delta$=0.88 for terminal $CH_3$ $\delta$=1.26, 1.61 and 1.97 for methylene groups of (—$CH_2$—C$H_2$—$CH_2$), ($CH_2$—$CH_2$—C=O) and (O—$CH_2$—C$H_2$—$CH_2$—O) respectively, $\delta$=2.28 for methylene group adjustcent to ester (C$H_2$—C=O)

$\delta$=4.15 for ester (C(=O)—O—$CH_2$—).

Proton NMR can distinguish the protons corresponding to the end groups ($CH_2$—OH) ($\delta$=3.7) from that of the middle ester groups ($CH_2$—O—C(=O)—) ($\delta$=4.15 and 4.24 for diester and monoester, respectively) and thus it is possible to identify ester and can monitor the reaction by comparing the integral areas of these two peaks.

$$\% \text{ Esterification} = \frac{\text{Combined areas of peaks at 4.15 and 4.24} \times 100}{\text{Combined areas of peaks at 3.70, 41.5 and 4.24}}$$

Example 1

Conversion of D-Glucose to 1,3-Propanediol Under Fermentation Conditions

*E. coli* strain ECL707, containing the *K. pneumoniae* dha regulon cosmids pKP1 or pKP2, the *K. pneumoniae* pdu operon pKP4, or the Supercos vector alone, is grown in a 5 L Applikon fermenter for the production of 1,3-propanediol from glucose.

The medium used contains 50-100 mM potassium phosphate buffer, pH 7.5, 40 mM (NH4)2SO4, 0.1% (w/v) yeast extract, 10 μM CoCl2, 6.5 μM CuCl2, 100 μM FeCl3, 18μ □M FeSO4, 5 μM H3BO3, 50 μM MnCl2, 0.1 μM Na2MoO4, 25 μM ZnCl2, 0.82 mM MgSO4, 0.9 mM CaCl2, and 10-20 g/L glucose. Additional glucose is fed, with residual glucose maintained in excess. Temperature is controlled at 37° C. and pH controlled at 7.5 with 5N KOH or NaOH. Appropriate antibiotics are included for plasmid maintenance. For anaerobic fermentations, 0.1 vvm nitrogen is sparged through the reactor; when the dO setpoint was 5%, 1 vvm air is sparged through the reactor and the medium is supplemented with vitamin B12.

Titers of 1,3-propanediol (g/L) range from 8.1 to 10.9. Yields of bio-PDO (g/g) range from 4% to 17%.

Example 2

Purification of Biosourced 1,3-Propanediol

Published U.S. Patent Application No. 2005/0069997 discloses a process for purifying 1,3-propanediol from the fermentation broth of a cultured *E. coli* that has been bioengineered to synthesize 1,3-propanediol from sugar. The basic process entails filtration, ion exchange and distillation of the fermentation broth product stream, preferably including chemical reduction of the product during the distillation procedure.

1,3-Propanediol, produced as recited in Example 1, was purified, by a multistep process including broth clarification, rotary evaporation, anion exchange and multiple distillation of the supernatant.

At the end of the fermentation, the broth was clarified using a combination of centrifugation and membrane filtration for cell separation, followed by ultrafiltration through a 1000 MW membrane. The clarified broth processed in a large rotary evaporator. Approximately 46 pounds of feed material (21,000 grams) were processed to a concentrated syrup. A 60 ml portion of syrup was placed in the still pot of a 1" diameter distillation column. Distillation was conducted at a vacuum of 25 inches of mercury. A reflux ratio of approximately 1 was used throughout the distillation. Several distillate cuts were taken, the central of which received further processing. The material was diluted with an equal volume of water, the material was loaded onto an anion exchange column (mixed bed, 80 grams of NM-60 resin), which had been water-washed. Water was pumped at a rate of 2 ml/min, with fractions being collected every 9 minutes. Odd number fractions were analyzed, and fractions 3 through 9 contained 3G. The fractions containing 3G were collected and subjected to microdistillation to recover several grams of pure 1,3-propanediol monomer (which was polymerized to mono and diesters according the methods described in Example 2-8).

Example 3

Production of Propanediol Distearate Using P-Toluenesulfonic Acid As Catalyst To prepare propanediol distearate from biosource 1,3-propanediol and stearic acid, biosource 1,3-propanediol was purified using methods as in examples 1 and 2. 2.58 g (0.033 moles) of biosource 1,3-propanediol, 19.45 g (0.065 moles) of stearic acid (Aldrich, 95%), and 0.2125 g (0.001 moles) of p-toluenesulfonic acid (Aldrich 98.5%) were charged into glass reactor fitted with mechanical stirrer and the reactor was flushed with dry nitrogen gas to remove air and moisture for 15 min. Then reaction temperature was raised to 100° C. while thoroughly stirring the reaction mixture under nitrogen flow and continued for 210 min.

After completion of the reaction, reaction mixture was cooled to about 35° C. and the product was transferred into a beaker. The product was purified by adding 100 mL of water and thoroughly stirring at 45-60° C., to form an emulsion for 15 min. The mixture was cooled and the solid propanediol distearate was separated by filtration.

The product was characterized by $^1$H NMR (Nuclear Magnetic Resonance) spectra (CDCl$_3$ (deuterated chloroform)): δ=0.88 (t, CH$_3$—CH$_2$, 6H), 1.26 (t, CH$_2$—CH$_2$—CH$_2$, 28H), 1.61 (t, $\overline{CH_2}$—CH$_2$—C=O, 4H), 1.97 (t, $\overline{\phantom{-}}$O—CH$_2$—CH$_2$—CH$_2$=O, 2H), 2.28 (t, CH$_2$—C=O, 4H), 4.15 (t, $\overline{C}$(=O)—O—CH$_2$— 4H) and $\overline{DSC}$ (T$_m$=66.4° C. and Tc=54.7° C.).

Example 4

Purity Characterizations of Biologically-Derived 1,3-Propanediol

In Table 1 below, biologically-derived 1,3-propanediol (produced and purified as described in Published U.S. Patent Application No. 2005/0069997) ("Bio-PDO") is compared, in several purity aspects, to two separate commercially-obtained preparations of chemically-produced 1,3-propanediol (Source A and B).

TABLE 1

|  | Units | Source A | Source B | Bio-PDO |
| --- | --- | --- | --- | --- |
| Total Org Impurities | ppm | 570 | 695 | 80 |
| UV Abs 220 nm, | AU | 0.25 | 1.15 | 0.12 |
| UV Abs 250 nm, | AU | 0.123 | 0.427 | 0.017 |
| UV Abs 275 nm | AU | 0.068 | 0.151 | 0.036 |
| UV Abs 350 nm | AU | 0.013 | 0.007 | 0.001 |
| Peroxides | ppm | 67 | 43 | 2 |
| CIE L*a*b* ASTM D6290 | b* | 0.411 | 0.03 | 0.1 |
| Carbonyls | ppm | 147 | 175 | 1 |

A typical profile of purity aspects are provided in Table 2 below, on a sample of biologically-produced 1,3-propanediol purified by a process disclosed in Published U.S. Patent Application No. 2005/0069997.

TABLE 2

|  | Units |  |
| --- | --- | --- |
| 1,3-Propanediol | GC area % | 99.992 |
| pH, neat | pH | 8.22 |
| UV Abs. @ 270 nm, 1:5 dilution | AU | 0.01 |
| Color APHA |  | 3 |
| Color (Process Measurement) L*a*b* | b* | 0.10 |
| Water | ppm | 115 |
| UV abs 220 nm neat | AU | 0.144 |
| UV abs 250 nm neat | AU | 0.017 |
| UV abs 275 nm neat | AU | 0.036 |
| UV abs 350 nm neat | AU | 0.001 |
| Peroxide | ppm | 2 |
| Metals | ppm | <1 |
| Sulfur | ppm | <1 |
| Carbonyl | ppm | 1 |

The unit ppm of total organic impurities means parts per million of total organic compounds in the final preparation, other than 1,3-propanediol, as measured by a gas chromatograph with a flame ionization detector. Results are reported by peak area. A flame ionization detector is insensitive to water, so the total impurity is the sum of all non 1,3-propanediol organic peaks (area %) ratioed to the sum of all area % (1,3-propanediol included). The term "organic materials" refers to the contaminants containing carbon.

The tables show that the disclosed method of purification provides for highly pure biologically derived 1,3-propanediol, as compared to commercially-obtained preparations of chemically-produced 1,3-propanediol.

Example 5

Skin Irritation and Sensitization Characterization of Biologically-Derived 1,3-Propanediol In a human skin patch test with approximately 100 subjects, 5, 25, and 50% PDO did not cause any skin reactions indicative of irritation or sensitization. A second human skin patch test did not produce any clinically significant dermal irritation or sensitization reactions with concentrations of 25, 50, and 75% PDO at pH 7, or 75% PDO at pH 4 and 9. Based on these studies PDO is not expected to be a skin irritant or sensitizer in humans. In the second human skin patch test, propylene glycol (1,2-propanediol or PG) was also tested at 25, 50, and 75% (pH 7) and all three concentrations of PG were patch test irritants and cumulative irritants for human skin.

Examples 6-8 are prophetic and are based on a descriptions from: D'Amelio, Frank S Sr.; *Botanicals: A Phytocosmetic Desk Reference*; CRC Press 1999, pg. 299-304.

Example 6

A Natural, High Foaming, Gentle Shampoo for Everyday Use

| Percent | Sequence | Raw Material | INCI Name |
| --- | --- | --- | --- |
| 1.00 | 1 | Deionized Water | Water |
| 0.00 | 1 | Saponins | Saponins |
| 0.00 | 1 | Cocamidopropyl Betaine | Cocamidopropyl Betaine |
| .00 | 1 | Cocamide DEA 1:1 | Cocamide DEA |
| .10 | 1 | Horsetail Extract, 5:1 BIO-PDO | Horsetail Extract |
| .10 | 1 | Comfrey Leaf Extract, 5:1 BIO-PDO | Comfrey Leaf Extract |
| .10 | 1 | Rosemary Extract, 5:1 BIO-PDO | Rosemary Extract |
| .10 | 1 | Chamomile Extract, 5:1 BIO-PDO | *Matricaria* Extract |
| .s. | 2 | 50% Aq. Sodium Hydroxide | Sodium Hydroxide |
| .50 | 3 | Aculyn 22 Thickener[1] | Acrylates/Steareth-20 Methacrylate Copolymer |
| 5.00 | 4 | Plantaren 2000[2] | Decyl Polyglucose |
| .10 | 4 | Lipovol A[3] | Avacado Oil |
| .s. | 5 | 25% Aqueous Citric Acid | Citric Acid |
| 0.00 | 6 | UCARE Polymer LR 30M (1.3%)[4] | Polyquaternium-10 |
| .00 | 7 | Lipamide MEAA[4] | Acetamide MEA |

Note:
5:1 Bio-PDO is defined as 5 parts biologically derived 1,3-propanediol with 1 part dehydrated botanical. (20% of a 1:1 extract)
[1]Rohm & Haas
[2]Henkel
[3]Lipo Chemicals, Inc.
[4]Amerchol Procedure:
1. Combine Sequence 1 ingredients at room temperature using a slow to moderate mixing to prevent aeration until homogeneous.
2. Adjust pH to 9.2 with Sequence 2 ingredient.
3. Slowly add Sequence 3 and continue mixing until polymer is completely dispersed.

4. Add Sequence 4 ingredients slowly and mix until homogeneous.
5. Adjust pH to 5.5 with Sequence 5 ingredient.
6. Add Sequence 6 slowly and mix until homogeneous.
7. Add Sequence 7 slowly and mix until homogeneous.

Example 7

All Natural Blooming Bath Oil

| Percent | Sequence | Raw Material | INCI Name |
|---|---|---|---|
| 15.96 | 1 | Lipovol ALM[5] | Sweet Almond Oil |
| 63.54 | 1 | Lipovol SES[1] | Sesame Oil |
| 5.00 | 1 | Lipolan R[1] | Lanolin Oil |
| 5.00 | 1 | Lipopeg 2-DL | PEG-4 Dilaurate |
| 10.00 | 1 | Lipocol 0-2[1] | Oleth-2 |
| 0.10 | 1 | Propylparaben | Propylparaben |
| 0.10 | 1 | Vitamin E USP-FCC[6] | Vitamin E |
| 0.10 | 2 | Arnica 5:1 BIO-PDO | *Arnica* Extract |
| 0.10 | 2 | Chamomile 5:1 BIO-PDO | Chamomile Extract |
| 0.10 | 2 | Comfrey 5:1 BIO-PDO | Comfrey Extract |
| q.s. | 3 | D & C Green #6 (0.5% Sol'n in BIO-PDO) | D & C Green #6 |

Note:
[5]:1 Bio-PDO is defined as 5 parts biologically derived 1,3-propanediol with 1 part dehydrated botanical. (20% of a 1:1 extract)
[5]Lipo Chemicals, Inc.
[6]Roche Vitamins and Fine Chemicals Procedure:
1. Combine Sequence 1 ingredients under vigorous mixing and heat to 557° C. until propylparaben is completely dissolved. Cool to 30° C.
2. At 30° C., add Sequence 2 ingredients to batch and cool to 25° C. At 25° C., add Sequence 3 until desired shade is obtained.

Example 8

High Humectant, Aqueous Spray-On Moisturizer

| Percent | Sequence | Raw Material | INCI Name |
|---|---|---|---|
| 92.70 | 1 | Deionized Water | Water |
| 2.00 | 1 | Lipocare HA/EC[7] | Echinacin |
| 5.00 | 1 | Liponic EG-1[1] | Glycereth-26 |
| 0.10 | 1 | Slippery Elm Bark 5:1 BIO-PDO[8] | Slippery Elm Extract |
| 0.10 | 1 | Chamomile Extract 5:1 BIO-PDO[2] | *Matricaria* Extract |
| 0.10 | 1 | Wild Alum Extract 5:1 BIO-PDO[2] | Cranesbill Extract |

Note:
5:1 Bio-PDO is defined as 5 parts biologically derived 1,3-propanediol with 1 part dehydrated botanical. (20% of a 1:1 extract)
[7]Lipo Chemicals, Inc.
[8]BioBotanica/Lipo Chemicals, Inc.

Procedure:
Combine ingredients under vigorous mixing at room temperature until batch is clear and uniform.

Example 9

Extraction of Chamomile Flower Powder by Bio-PDO and Bio-PDO Ester Mixture

Esters based on biologically-derived 1,3-propanediol were synthesized, purified and characterized as it is described in U.S. Provisional Patent application 60/772,112, filed Feb. 10, 2006, incorporated herein by reference.

Biologically-derived 1,3-propanediol and 1,3-propanediol conjugate ester were used for the extraction of Chamomile flower powder (*Martricaria recutita* from Egypt, distributor—Mountain Rose Herbs, Oreg.).

The Chamomile powder was mixed with 1,3-propanediol and macerated for 30 minutes on a shaking table, then 1,3-propanediol ester was added to the mixture and the temperature was raised to 90° C. and the maceration was continued for additional 2 hours. The material was filtered through a 0.2 μm GHP membrane and the filtrate was analyzed by LC/MS and shown to contain extracted compounds.

Example 10

Extraction of Chamomile Flower Powder by Bio-PDO Ester

The biologically-derived 1,3-propanediol conjugate ester was synthesized as it is written in Example 9 and the ester (Bio-PDO bis-ethylhexanoate) was used for the extraction of Chamomile flower powder (Mountain Rose Herbs, Oreg.).

The Chamomile powder was mixed with the ester and macerated for 2, 4, 6 hours on a shaking table. The material was filtered through a 0.2 μm GHP membrane and the filtrate was analyzed by UV/VIS (UV/Vis Spectrophotometer, Varian (Australia), Model: Cary 5000) and the spectra demonstrated that the efficacy of the extracted compounds was proportional with the time used for the maceration.

Example 11

Extraction of Red Roses by Bio-PDO Ester

The biologically-derived 1,3-propanediol conjugate ester was synthesized as it is written in Example 9 and the ester (Bio-PDO bis-ethylhexanoate) was used for the extraction of dried Red Roses (*Rosa centifolia*, Mountain Rose Herbs, Oreg.).

The dried roses was mixed with the ester and macerated for 2, 4, 6 hours on a shaking table. The material was filtered through a 0.2 μm GHP membrane and the filtrate was analyzed by UV/VIS.

Example 12

Extraction of Seaweed by Bio-PDO Ester

The biologically-derived 1,3-propanediol conjugate ester was synthesized as it is written in Example 9 and the ester (Bio-PDO bis-ethylhexanoate) was used for the extraction of dried seaweed (local farmers' market).

The dried seaweed was mixed with the ester and macerated for 2, 4, 6 hours on a shaking table. The material was filtered through a 0.2 μm GHP membrane and the filtrate was analyzed by UV/VIS.

Example 13

Botanical Extraction Using Bio-PDO/Methanol Mixture

Procedure: 5 g of dried Jasmine flower (*Jasminum officinale*, Mountain Rose Herbs, Oreg.) was immersed in the mixture of Bio-PDO/methanol (70%:30%) and macerated for 24 h. The material was filtered through a 0.2 μm GHP membrane and the filtrate was analyzed by LC/MS. The LC/MS spectra demonstrated the effective extraction of the active ingredients.

Example 14

Honeysuckle Flower Extraction Using Bio-PDO/Deionized Water Mixture

Procedure: 5 g of dried Honeysuckle flower (*Lonicera japonica*, origin China, distributor Mountain Rose Herbs, Oreg.) was immersed in the mixture of Bio-PDO/d.water (50%:50%) and macerated for 24 h. The material was filtered through a 0.2 μm GHP membrane and the filtrate was analyzed by LC/MS. The LC/MS spectra demonstrated the effective extraction of the active ingredients.

Example 15

Eucalyptus Leaf Extraction Using Bio-PDO/Deionized Water Mixture

Procedure: 5 g of dried Eucalyptus leaf (*Eucalyptus globulus*, origin France, distributor Mountain Rose Herbs, Oreg.) was immersed in the mixture of Bio-PDO/d.water (50%:50%) and macerated for 24 h. The material was filtered through a 0.2 μm GHP membrane and the filtrate was analyzed by LC/MS. The LC/MS spectra demonstrated the effective extraction of the active ingredients.

Example 16

Sandalwood Red Powder Extraction Using Bio-PDO/Deionized Water Mixture

Procedure: 5 g of dried Sandalwood Red Powder (*Pterocarpus santalinus*, origin Africa, distributor Mountain Rose Herbs, Oreg.) was immersed in the mixture of Bio-PDO/d.water (50%:50%) and macerated for 24 h. The material was filtered through a 0.2 μm GHP membrane and the filtrate was analyzed by LC/MS. The LC/MS spectra demonstrated the effective extraction of the active ingredients.

Comparative Example 1

Comparison Between Biologically Derived 1,3-Propanediol and Propylene Glycol in Plant Material Extractions Bio-1,3-propanediol and propylene glycol were used to extract ingredients from Jasmine flower, Chamomile flower powder (*Matricaria recutita*) myrrh gum cut benzoin gum powder, and bees wax. LC-MS and GC-MS were used to analyze the extracted ingredients. Qualitative analysis confirmed that ingredients extracted using 1,3-propanediol are same as those extracted using propylene glycol. Additionally, ingredients extracted using bio-1,3-propanediol and mixtures of bio-1,3-propanediol and methanol were the same.

The major ingredients of chamomile extraction are bisabolol oxide, en-in-dicyclo ether, and Apigenin glucoside. Comparitive yields of these active ingredients using 1,3-propanediol and propylene glycol (1,2-Propanediol, Aldrich) are shown below in Table 1:

TABLE 1

| Extract Product | Bio-1,3-propanediol Area | Propylene Glycol Area | % difference |
|---|---|---|---|
| Bisabolol oxide | 9217821[a] | 8760424[a] | 5.2 |
| Apigenin glucoside | 3972525[b] | 3549734[b] | 11.2 |
| en-in-dicyclo ethers | 9394370[b] | 7261956[b] | 29.2 |

[a]GC-MS analysis,
[b]LC-MS analysis

The table shows the GC-MS/LC-MS peak areas of the extracted ingredients using 1,3-propanediol and propylene glycol. Using Bio-1,3-propanediol the extraction process extracted 29.4 wt % higher en-in-cycloethers, 11.2 wt % higher apigenin glucoside, and 5.2 wt % higher bisabolol oxide as compared to the extraction using propylene glycol.

Comparative Example 2

Chamomile flower powder (5 g) was mixed with 50 g of solvent mixture (Bio-PDO/Deionized Water, ratio 1:1, and also the mixture of 1,2-Propanediol (Propylene glycol, Aldrich)/Deionized Water, ratio 1:1). The mixture was kept for agitation for 24 h. The extract was filtered and analyzed.

TABLE 2

Comparison of extraction of Chamomile using Bio-PDO and Propylene glycol

| Product | Bio-PDO/ Water Area | Propylene glycol/ Water Area | % Difference |
|---|---|---|---|
| Bisabolol oxide | 25176422 | 14409166 | 75 |
| Apigenin | 2374215 | 556691 | 326 |
| Apigenin glucoside | 658824 | 420412 | 57 |
| en-in-dicyclo ethers | 1842764 | 866635 | 113 |

The data in Table 2. show the GC-MS/LC-MS peak areas of the extracted ingredients using Bio-PDO/water and propylene glycol/water mixtures. Using Bio-PDO/water mixture 75 wt % higher Bisabolol oxide, 326 wt % higher Apigenin, 113 wt % higher en-in-cycloethers, 57 wt % higher apigenin glucoside were extracted than those extracted using propylene glycol.

Comparative Example 3

Hamomile flower powder (Mountain Rose Herb, Oreg.) (5 g) was mixed with 50 g of Bio-PDO also 5 g of Chamomile flower powder was mixed with Deionized Water. The mixture was macerated for 24 h. The extract was filtered and analyzed by LC/MS.

TABLE 3

Comparison of extraction of Chamomile using Bio-PDO and Water

| Product | Bio-PDO/Area | H$_2$O/Area | % Difference |
|---|---|---|---|
| Apigenin | 63.32 | 125.53 | −50.4 |
| Apigenin glucoside | 134.58 | 0 | |
| en-in-dicyclo ethers | 1340.74 | 0 | |

Using deionized water apigenin glucoside and en-in-dicyclo ethers were not extracted though apigenin extraction was higher compared to that using Bio-PDO.

Example 17

Biologically-Derived 1,3-Propanediol in Cosmetic Emulsion

| Ingredients: | % Wt. |
|---|---|
| Phase A | |
| Water, deionized | 61.34 |
| Tetrasodium EDTA | 0.10 |
| Bio-PDO ™ (E.I. du Pont de Nemours and Company ("DuPont"), Wilmington, Del.) | 5.00 |
| Carbopol 980 (2% solution) | 10.00 |
| Phase B | |
| Puresyn ® | 25.00 |
| Lipomulse ® 165 | 2.50 |
| Stearic Acid XXX | 2.50 |
| Cetearyl Alcohol | 0.50 |
| Dimethicone DC 200-100 | 1.00 |
| Phase C | |
| NaOH (20% solution) qs to pH 7.0-7.5 | 1.06 |
| Phase D | |
| Germaben II | 1.00 |

Phase A was combined at 75° C. Phase B was combined at 75° C. Phase B was added to Phase A. Phase C was then added to the Phase A/B. Phase A/B/C was cooled to 40° C. and then Phase D was added. pH was adjusted to 7.0-7.5 with Phase C. The formulation produced was a smooth white and apparently stable emulsion.

RESULTS—pH 7.38, viscosity 12000 cps at 20 RPM. Oven stability was examined. Results were deemed acceptable. Freeze/thaw stability was also examined. Freeze/thaw stability was deemed acceptable.

Comparative Examples 4-6

Cosmetic Emulsions Containing Other Polyols

For comparative purposes, cosmetic emulsions containing other polyols were also produced as described in Example 17, except that the biologically-derived 1,3-propanediol was substituted with propylene glycol, 1,3-butylene glycol, or 2-methyl-1,3-propanediol. The cosmetic emulsions containing propylene glycol, 1,3-butylene glycol, or 2-methyl-1,3-propanediol were stable.

The viscosity of the cosmetic emulsion containing biologically-derived 1,3-propanediol was on par with that of propylene glycol (12600 cps) and higher than that of 1,3-butylene glycol (6000 cps) or 2-methyl-1,3-propanediol (9600 cps).

Example 18

Skin Irritation Characterization of Biologically-Derived 1,3-Propanediol

The purpose of this study was to determine the potential of biologically-derived 1,3-propanediol, diluted to concentrations of 5%, 25%, and 50%, to cause irritation or delayed contact hypersensitivity in humans. The method employed in carrying out this test, described below, was similar to that described in "Appraisal of the Safety of Chemicals in Foods, Drugs and Cosmetics" by J. H. Drake and published by the Association of Food and Drug Officials of the United States, incorporated herein by reference.

Test Panel: The test involved the application of the test article to the upper arms of a group of 112 volunteer panelists. The panelists ranged from 16 to 71 years of age. One hundred and five panelists completed the study. Prior to the initiation of the study, all panelists were in good general health and free of any visible skin disease or anomaly in the area to be patched. Each panelist was required to read, understand and sign an informed consent statement.

Patch Preparation: The test articles (biologically-derived 1,3-propanediol diluted with D.I. water to a concentration of 5%, diluted with D.I. water to a concentration of 25%, and diluted with D.I. water to a concentration of 50%) were applied (0.1 mL) to a one-inch Lintine® Disk (Filter Fabrics, Goshen, Md.) and placed onto a strip of 2 inch Dermicel® hypoallergenic cloth tape (Johnson & Johnson, New Brunswick, N.J.). Before applying this strip, each portion of test material was secured in place with a gloved finger to insure proper application. This tape strip was then pressed into place on the upper left arm of each panelist at its designated test site.

Induction Phase: These patches were applied to their designated contact sites and remained in place for 24 hours. At the end of this period, the patches were removed and the sites were examined for any dermal response. The panelists were then rested for a 24-hour period after which the skin sites were again examined. New patches were then applied to the same sites as previously used. The second applications were identical to the first and remained in place 24 hours. This procedure was repeated on Mondays, Wednesdays and Fridays until a series of nine applications had been made. Patch applications made on Friday were removed by the panelists on Saturday. The panelists examined the sites (with assistance if necessary) for any dermal response at the time of removal and again at 48 hours and reported their observations prior to the next application. The same sites were used throughout the study. In the event when one induction application was missed, the panelist was allowed to make it up at the end of the induction patch period. These patches were applied on Monday following the last scheduled (ninth) induction application on Friday.

Challenge Phase: After the 9th application, a rest period of approximately 2 weeks elapsed after which a challenge application was applied in the same manner and to the same sites described above.

Based upon the effects observed with the test materials placed repeatedly on the skin during both the induction and challenge phases, biologically-derived 1,3-propanediol, diluted to concentrations of 5%, 25%, and 50%, is considered not to be a skin irritant, fatiguing agent, or sensitizing agent under the conditions that prevailed in this study.

Example 19

Clear Face and Hand Lotion

| Ingredients: | % Wt. |
|---|---|
| Deionized water | 66.20 |
| Bio-PDO ™ (DuPont) | 16.00 |
| Ritasail 190 (RITA) (dimethicone copolyol) | 2.00 |

-continued

| Ingredients: | % Wt. |
|---|---|
| Pationic ® 122A (RITA) (sodium caproyl lactylate 21.1% aqueous) | 3.80 |
| Rhodapex ® ESY (Rhodia) (sodium laureth sulfate 26% aqueous) | 4.00 |
| Germaben II (ISP/Sutton) (propylene glycol, diazolidinyl urea, methylparaben and propylparaben) | 1.00 |
| Tetrasodium EDTA 5% aqueous | 1.00 |
| Aculyn ® 22 (ISP/Rohm & Haas) (acrylates/steareth-20 methacrylate copolymer 25% aqueous) | 5.00 |
| Triethanolamine | 1.00 |
| Fragrance | q.s. |

Procedure: Ingredients are combined in order as listed. Properties: pH: 7.0, viscosity: 6,780 cps Example 20

Hand and Body Cream

| Ingredients: | % Wt. |
|---|---|
| Deionized water | 75.49 |
| Cellosize ® PCG 10 (Amerchol) | 0.20 |
| Trisodium EDTA (Universal Preserv-A-Chem) | 0.10 |
| Bio-PDO ™ (DuPont) | 6.50 |
| Shebu ® Refined (RITA) (shea butter) | 2.00 |
| Arlacel ® 60 (Uniqema) | 4.00 |
| MYRJ ® 52S (Uniqema) | 0.50 |
| Glycol stearate (Stepan) | 2.00 |
| DC SF 200/350 (Dow Corning) | 4.00 |
| Isopropyl palmitate (Stepan) | 3.00 |
| Vitamin A palmitate (Roche) | 0.01 |
| *Aloe vera* gel (Bio-Botanica) | 0.50 |
| Cucumber extract (Bio-Botanica) | 0.50 |
| *Ginkgo biloba* extract (Bio-Botanica) | 0.50 |
| Red clover extract (Bio-Botanica) | 0.50 |
| Biopein ® (Bio-Botanica) | 0.20 |

Procedure: Disperse Cellosize® PCG 10 into deionized water with mixing. Add trisodium EDTA and Bio-PDO™ with mixing and heat to 80° C. Add the next seven items and continue mixing until uniform. Remove heat and allow to cool. At 30° C., add aloe vera gel, cucumber extract, *ginkgo biloba* extract and red clover extract. Add Biopein® and mix until homogenous.

Example 21

Moisturizing Body Care Cream

| Ingredients: | % Wt. |
|---|---|
| Phase A | |
| Cremophor ® A6 (BASF) (ceteareth-6) | 2.0 |
| Cremophor ® A25 (BASF) (ceteareth-25) | 2.0 |
| *Vitis vinifera* (grape) seed oil | 6.0 |
| Glyceryl Stearate SE | 3.0 |
| Cetearyl alcohol | 2.0 |
| Dimethicone | 0.5 |
| Luvitol EHO (BASF) (cetearyl octanoate) | 8.0 |
| Oxynex ® 2004 (Merck KgaA) (1,3-Propanediol, BHT, ascorbyl palmitate, glyceryl stearate and citric acid) | 0.1 |

| Ingredients: | % Wt. |
|---|---|
| Phase B | |
| Bio-PDO ™ (DuPont) | 5.0 |
| Edeta BD (BASF) (disodium EDTA) | 0.1 |
| D-Panthenol USP (BASF) | 1.0 |
| Preservative | q.s. |
| Water | q.s. to 100 |
| Phase C | |
| Luvigel EM (BASF) (caprylic/capric triglycerides and sodium acrylates copolymer) | 1.0 |
| Phase D | |
| Vitamin E Acetate (BASF) | 0.5 |
| Perfume | q.s. |

Procedure: Heat phase A and phase B to about 80° C. Stir phase B into phase A while homogenizing. Add phase C to phase A/B and homogenize again. Cool to about 40° C., add phase D and homogenize shortly. Properties: Viscosity: approx. 25,000 mPa·s (Brookfield); pH value: 6.5

Example 22

Moisturizing Body Care Cream

| Ingredients: | % Wt. |
|---|---|
| Phase A | |
| Cremophor ® GC 7 (BASF) (PEG 7-glyceryl-cocoate) | 8.0 |
| Cremophor ® A-25 (BASF) (ceteareth-25) | 22.0 |
| Cremophor ® WO 7 (BASF) (hydrogenated castor oil) | 1.0 |
| Bio-PDO ™ (DuPont) | 3.0 |
| Masil ® SF19 (BASF) (PEG 8 methicone) | 1.0 |
| Phase B | |
| Water | 65.0 |
| Phase C | |
| Preservative | q.s. |
| Fragrance | q.s. |

Procedure: Add ingredients in above order at 80° C. and mix until uniform. Assure each is dissolved prior to next addition. Heat phase B to 80° C. and combine with phase A. Cool to 50° C. Add fragrance and preservative. Pour into containers while liquid and allow to set at room temperature.

Example 23

Moisturizing Hand and Body Lotion

| Ingredients: | % Wt. |
|---|---|
| Phase A | |
| Varisoft ® TA-100 (Goldschmidt) (distearyldimonium chloride) | 4.75 |
| Crodacol C-70 (Croda) (cetyl alcohol) | 2.00 |
| Penreco Snow White Petrolatum (Penreco) (petrolatum) | 4.00 |
| DC Fluid 200, 1,000 cst (Dow Corning) (dimethicone) | 0.25 |

-continued

| Ingredients: | % Wt. |
|---|---|
| Phase B | |
| Deionized water | q.s. |
| Stepan ® IPM (Stepan) (isopropyl myristate) | 3.25 |
| Bio-PDO ™ (DuPont) | 4.00 |
| Phase C | |
| Sensomer ® CI-50 (Ondeo Nalco) (starch hydroxypropyltrimonium chloride) | 3.00 |
| AA040513 Cucumber (Arylessence) (fragrance) | 0.25 |
| Preservative | q.s. |
| Sodium hydroxide | q.s. to pH 6 |

Procedure: In separate containers, thoroughly mix the ingredients of phase A and phase B to 75° C. Pour phase A into phase B; mix well at temperature for 10 minutes. Remove heat and continue mixing until temperature is under 40° C. Add phase C ingredients in the order listed, mixing well between additions. Adjust pH to 6.

Example 24

Moisturizing Lotion SPF15

| Ingredients: | % Wt. |
|---|---|
| Phase A | |
| Stearyl alcohol | 2.00 |
| Estol ® 1543 (Uniqema) (ethylhexyl palmitate) | 5.00 |
| Estol ® 3609 (Uniqema) (triethylhexanoin) | 5.00 |
| Tween ® 60 (polysorbate 60) | 2.00 |
| Isohexadecane | 7.50 |
| Solaveil ® CT100 (Uniqema) (C12-C15 alkyl benzoate (and) titanium dioxide (and) polyhydroxystearic acid (and) aluminum stearate (and) alumina) | 15.00 |
| Phase B | |
| Distilled water | 54.40 |
| Arlatone ® 2121 (Uniqema) (sorbitan stearate (and) sucrose cocoate) | 2.50 |
| Monomate RMEA-40 (aqua (and) disodium ricinoleamido MEA-sulfosuccinate) | 0.200 |
| Phase C | |
| Veegum ® Ultra (RT Vanderbilt) (magnesium aluminum silicate) | 0.80 |
| Keltrol ® RD (Nutrosweet Kelco) (xanthan gum) | 0.20 |
| Sodium lactate 50% | 0.40 |
| Germaben ® II (ISP) (propylene glycol (and) diazolidinyl urea (and) methylparaben (and) propylparaben) | 1.00 |
| Bio-PDO ™ (DuPont) | 4.00 |

Procedure: Heat phase B to 80° C. with moderate stirring, until Arlatone® 2121 is fully dispersed. Add Keltrol® and Veegum®; stir until homogeneous. Add remaining water phase ingredients, maintaining temperature at 80° C. Heat phase A to 80° C. Add phase A to B/C with vigorous mixing. Homogenize for two minutes. Cool with moderate stirring to room temperature.

Example 25

Skin Treatment Lotion

| Ingredients: | % Wt. |
|---|---|
| Phase A | |
| Deionized water | 61.7 |
| Keltrol ® CG (Kelco) (xanthan gum) | 0.2 |
| Bio-PDO ™ (DuPont) | 5.0 |
| Multifruit ® BSC (Arch Personal Care) | 3.0 |
| Jeescreen Benzophenone-4 (Jeen) (benzophenone-4) | 0.1 |
| Jeechem GMS-165 (Jeen) (glyceryl stearate (and) PEG-100 stearate) | 3.0 |
| Phase B | |
| Jeesilc IDD (Jeen) (dimethicone crosspolymer-3 (and) isododecane) | 4.0 |
| Jeesilc 245 (Jeen) (cyclomethicone) | 8.0 |
| Jeesilc 200 MV (100 cst) (dimethicone) | 2.0 |
| Simulgel ® NS (Seppic) | 4.0 |
| Phase C | |
| Jeesilc 6056 (Jeen) (dimethylpolysiloxane gum) | 3.0 |
| Jeecide G-II (Jeen) (propylene glycol (and) diazolidinyl urea (and) methylparaben (and) propylparaben) | 1.0 |
| *Arnica* Extract (Botanicals Plus) (*arnica montana*) | 2.0 |
| Flamingo Super Red | 1.0 |
| Phase D | |
| Jeesorb L-20 (Jeen) (polysorbate 20) | 1.0 |
| Vitamin E Acetate (Jeen) (tocopheryl acetate) | 0.5 |
| Fragrance | 0.5 |

Procedure: Heat water to 65° C. Pre-mix Keltrol® and Bio-PDO™ and add to the water phase. Mix until dissolved. Add the other ingredients of phase A one at a time and mix well. Cool to 50° C. In the oil phase tank, add the Jeesilc IDD, Jeesilc 245 and Jeesilc 200 MV (100 cst) and mix until uniform. Add the Simulgel® and mix to 50° C. Using a homogenizer, add phase B to phase A and mix for 10 minutes. Cool to 40° C. Switch to prop agitation. Add the ingredients of phase C one at a time into the main tank and mix well after each addition. Pre-mix phase D in a side vessel and add to the main tank. Mix well.

Example 26

Broad Spectrum SPF Sunscreen

| Ingredients: | % Wt. |
|---|---|
| Phase A | |
| Deionized water | 57.85 |
| Carbopol 980 (Noveon) (carbomer) | 0.30 |
| Disodium EDTA (Dow Chemical) | 0.10 |
| Bio-PDO ™ (DuPont) | 4.00 |
| Phase B | |
| Escalol 557 (ISP) (octinoxate) | 7.50 |
| Escalol 567 (ISP) (oxybenzone) | 6.00 |
| Escalol 517 (ISP) (avobenzone) | 2.00 |
| X-Tend 226 (ISP) (2-phenylethyl benzoate) | 10.00 |

-continued

| Ingredients: | % Wt. |
|---|---|
| Prolipid ® 141 (ISP) (glyceryl stearate, behenyl alcohol, palmitic acid, stearic acid, lecithin, lauryl alcohol, myristyl alcohol and cetyl alcohol) | 4.00 |
| Phase C | |
| Deionized water | 5.00 |
| Triethanolamine 99% | 0.40 |
| Phase D | |
| Liquapar Optima (ISP) (phenoxyethanol, methylparaben, isopropylparaben, isobutylparaben and butylparaben) | 1.25 |
| Liquapar Oil (ISP) (isopropylparaben, isobutylparaben and butylparaben) | 0.40 |
| Lexguard O (Inolex) (caprylyl glycol) | 1.00 |
| Phase E | |
| Glycacil ®-L (Lonza) (iodopropynyl butylcarbamate) | 0.20 |

Procedure: Combine ingredients in phase A; mix until uniform and heat to 75° C. Combine ingredients in phase B; heat to 75° C. Combine phase B with phase A with homogenization. Combine phase C with phase A/B with homogenization. Cool to 45° C. (heat Lexguard O and add to LiquaPar Optima) and add phase D. Add phase E. Cool to room temperature. Qs for water loss.

Properties: Viscosity: 17,600 cps, pH 6.44

Example 27

Water-Resistant Sunscreen Lotion SPF 21

| Ingredients: | % Wt. |
|---|---|
| Phase A | |
| Deionized water | 63.10 |
| Versene ® NA (Dow) (disodium EDTA) | 0.05 |
| Carbopol Ultrez 10 Polymer (Noveon) (carbomer) | 0.25 |
| Pemulen ® TR-2 Polymeric Emulsifier (Noveon) (acrylates/C10-30 alkyl acrylate crosspolymer) | 0.15 |
| Bio-PDO ™ (DuPont) | 3.00 |
| Phase B | |
| NeoHeliopan, Type AV (Haarmann & Reimer) (octyl methoxycinnamate) | 5.00 |
| Octyl salicylate | 3.00 |
| HallBrite ® BHB (C.P. Hall) (butyloctyl salicylate) | 5.00 |
| Parsol ® 1789 (Roche) (avobenzone) | 3.00 |
| Procol CS-20-D (Protameen) (cetearyl alcohol and ceteareth-20) | 1.50 |
| Crodamol CAP (Croda) (cetearyl octanoate) | 2.00 |
| Vitamin E acetate (BASF) | 0.50 |
| Phase C | |
| Crovol A-70 (Croda) (PEG-60 almond glycerides) | 0.50 |
| DC 1401 Fluid (Dow Corning) (dimethiconol and cyclomethicone) | 1.50 |
| Ultrasil Copolyol-1 Silicone (Noveon) (PEG-8 dimethicone) | 1.50 |
| Phenonip ® (Clariant) (phenoxyethanol, methylparaben, ethylparaben, propylparaben, butylparaben and isobutylparaben) | 1.00 |
| Tapioca Pure (National Starch) (tapioca starch) | 4.00 |
| Sodium hydroxide 18% | 1.00 |
| Avalure ® UR 450 Polymer (Noveon) (PPG-17/IPDI/DMPA copolymer 38% solids) | 3.95 |

Procedure: Dissolve disodium EDTA in warm water (~50° C.). Add Carbopol Ultrez 10 polymer and allow to wet out for approximately five minutes. Disperse Pemulen® Polymeric emulsifier and allow to mix in for about 15 minutes. Add Bio-PDO™. Bring phase A to ~70° C. Add approximately 15% of the total neutralizing agent necessary to phase A. Blend phase B ingredients and bring to ~80° C., making sure solid ingredients are dissolved. Add phase B to phase A with vigorous agitation. Add PEG-60 almond glycerides. Add dimethiconol and cyclomethicone. Add Ultrasil Copolyol-1 silicone. Add Phenonip® after the emulsion cools to <60° C. Add tapioca starch. Add the remainder of the neutralizing agent. Add Avalure® UR 450 polymer.

Properties: Appearance: white, creamy emulsion pH: 7.0-7.5

Viscosity (mPa·s)*: 15,000-21,000

SPF (waterproof)**: 21 (in-vitro method, 80 min. immersion)

Example 28

Waterproof Protective Suncare SPF 20

| Ingredients: | % Wt. |
|---|---|
| Phase A | |
| Simusol 165 (Seppic) (glyceryl stearate and PEG-100 stearate) | 3.20 |
| Montanov ® S (Seppic) (coco-glucoside and coconut alcohol) | 1.30 |
| Isodecyl neopentanoate | 10.00 |
| PVP hexadecene copolymer | 5.00 |
| Bio-PDO ™ (DuPont) | 5.00 |
| Ethyl hexyl methoxycinnamate | 7.50 |
| Benzophenone-3 | 2.50 |
| Ethyl hexyl salicylate | 5.00 |
| Zinc oxide | 7.10 |
| Phase B | |
| Sepicalm VG (Seppic) (sodium palmitoyl proline and *Nymphea alba* flower extract) | 3.00 |
| Cyclomethicone | 5.00 |
| Phase C | |
| Simulgel ® EG (Seppic) (sodium acrylate/acryloyldimethyltaurate copolymer, isohexadecane and polysorbate 80) | 1.00 |
| Phase D | |
| Tromethamine | q.s. |
| Tetrasodium EDTA | 0.20 |
| Xanthan gum | 0.15 |
| Magnesium aluminum silicate | 1.00 |
| Water | q.s. to 100 |
| Phase E | |
| Sepicide HB (Seppic) (phenoxyethanol (and) methylparaben (and) ethylparaben (and) propylparaben (and) butylparaben) | 0.30 |
| Sepicide CI (Seppic) (imidazolidinyl urea) | 0.20 |
| DL-alpha tocopherol | 0.05 |
| Fragrance | 0.30 |

Procedure: Melt phase A ingredients at 75-80° C. and disperse zinc oxide in the warm fatty phase. Disperse silicate and xanthan gum in water until homogeneous, then introduce EDTA and tromethamine. Add Simulgel® EG to this blend with vigorous stirring to obtain swelling of the polymer, then heat to 80° C. Add fatty phase A to the water phase and begin homogenizing for five minutes. Start cooling while continuously homogenizing. Introduce Sepicalm VG and cyclomethicone at 60° C. and homogenize for five minutes. Cool with moderate stirring and add phase E ingredients at 30° C.

Example 29

Hand Barrier Cream

| Ingredients: | % Wt. |
|---|---|
| Phase 1 | |
| D.I. Water | q.s. to 100.0 |
| Bio-PDO ™ (DuPont) | 4.00 |
| Ammonyx ® GA-70PG* | 2.86 |
| Phase 2 | |
| Petrolatum | 4.00 |
| Stepan ® IPP | 3.00 |
| Stepan ® Cetyl Alcohol, NF | 2.00 |
| TiO2Sperse 40% solution in Octyldodecyl Neopentanoate (Collaborative Labs) | 10.00 |
| Phase 3 | |
| KCl | 0.40 |
| Citric Acid | q.s. |
| Preservatives | q.s. |
| Total | 100.00 |

Procedure: Prepare water phase by adding water, Bio-PDO™ and Ammonyx® GA-70PG*. Mix well. Start heating to 160° F. Prepare oil phase by adding Petrolatum, Stepan® IPP, Stepan® Cetyl Alcohol and TiO2Sperse. Heat to 160-165° F. Add oil phase to the water phase. Emulsify for 20-25 minutes. Cool to room temperature. Premix KCl with water and add to batch. Add preservatives. Adjust pH to 4.0 if necessary.

Physical Properties 4.0-5.0; 2,000-3,000 cps

Example 30

Lotion for Normal-Oily Skin

| Ingredients: | % Wt. |
|---|---|
| Phase 1 | |
| D.I. Water | q.s. to 100.0 |
| Carbopol 934 (BF Goodrich) Carbomer | 0.15 |
| Bio-PDO ™ (DuPont) | 3.00 |
| Phase 2 | |
| Stepan ® Octyl Isononanoate | 5.00 |
| Dow Corning 200 Fluid (Dow Corning) Dimethicone | 0.10 |
| Wecobee ® S | 0.50 |
| Stepan ® Cetyl Alcohol, NF | 0.50 |
| Kartacid 1890 (Akzo Nobel BV) Stearic Acid | 3.00 |
| Phase 3 | |
| Versene ® 200 (Dow Corning) Tetrasodium EDTA | 0.10 |
| Triethanolamine | 1.80 |
| Preservative | q.s. |
| Total | 100.0 |

Procedure: Prepare Phase 1 by adding D.I. water to a suitable mixing vessel and begin agitation. Add Carbopol 934 with good agitation and mix at high speed until the solution is free of lumps. Add Bio-PDO™ and mix. Heat to 165-170° F. In a separate container prepare Phase 2 and heat to 170-175° F. Add Phase 2 to Phase 1 with good agitation and mix for 30 minutes. Start cooling to 90° F. At 110° F. add Phase 3 ingredients. Stop cooling and agitation at 90° F.

Properties: Viscosity at 25° C.: 2000-5000 cps; pH 7.8-8.0

Example 31

Skin Soothing Lotion

| Ingredients: | % Wt. |
|---|---|
| Phase 1 | |
| D.I. Water | q.s. to 100.0 |
| Carbopol 940 (B.F. Goodrich) Carbomer | 0.20 |
| Glucam ® P-20 (Amerchol) PPG-20 Methyl Glucose Ether | 0.14 |
| Bio-PDO ™ (DuPont) | 2.25 |
| Phase 2 | |
| Neobee ® M-20 | 4.50 |
| Wecobee ® S | 0.75 |
| Stepan ® 653 | 0.50 |
| Stepan ® Cetyl Alcohol, NF | 0.50 |
| Kartacid 1890 (Akzo Nobel BV) Stearic Acid | 2.95 |
| Phase 3 | |
| Preservative | 0.10 |
| Versene ® 220 (Dow) Tetrasodium EDTA | 0.10 |
| Triethanolamine | 0.25 |
| Total | 100.0 |

Procedure: Prepare Phase 1. Add Carbopol 940 to D.I. water with good mixing until solution is free of lumps. Add PPG-20 methyl glucose ether and Bio-PDO™. Mix until completely dissolved. Heat to 165° F. In a separate container, prepare Phase 2. Heat to 165-170° F. Add Phase 2 to Phase 1 (both at 165-170° F.) with good agitation. Emulsify for 20 minutes and then begin to cool with slow agitation. At 110° F. add ingredients from Phase 3. At 90° F. stop cooling and agitation.

Properties: Viscosity: at 25° C.: 2200-3700 cps

Example 32

Clear Moisturizer

| Ingredients: | % Wt. |
|---|---|
| *Aloe Vera* Gel | q.s. to 100.0 |
| Bio-PDO ™ (DuPont) | 3.50 |
| Methyl Paraben | 0.15 |
| Carbopol 934 | 0.50 |
| Alcohol 190 Proof | 20.00 |
| Stepan ® PEG 600 ML | 1.00 |
| Tween ® | 2.00 |
| Fragrance | q.s. |
| TEA 88% | 0.8 |
| Glydant | q.s. |
| Total | 100.0 |

Procedure: Combine Aloe Vera Gel and Bio-PDO™. Start mixing. Add methyl paraben. Mix until solution is clear. Add Carbopol 934. Mix until solution does not have lumps. Add alcohol. Mix well. Premix PEG 600 Monolaurate, Tween 20 and perfume. Add to batch. Mix well. Add Glydant. Add TEA. Solution should be clear.

Physical Properties: pH 6.0-6.5

Example 33

Therapeutic Hand & Body Lotion

| Ingredients: | % Wt. |
|---|---|
| Phase 1 | |
| D.I. Water | q.s. to 100.0 |
| Bio-PDO ™ (DuPont) | 4.00 |
| Ammonyx ® GA-70PG | 18.4 |
| Phase 2 | |
| Petrolatum | 4.0 |
| Stepan ® IPP | 3.0 |
| Silicone DC-200 (350 cps) | 1.0 |
| Stepan ® Cetyl Alcohol, NF | 2.0 |
| Phase 3 | |
| KCl | 0.4 |
| Citric Acid | q.s. |
| Glydant | q.s. |
| Total | 100.0 |

Procedure: Prepare water phase by adding water, Bio-PDO™, and Ammonyx® GA-70PG. Mix well. Start heating to 160° F. Prepare oil phase by adding petrolatum, Stepan® IPP, silicone, Stepan® Cetyl Alcohol. Heat to 160-165° F. Add oil phase to water phase. Emulsify for 20-25 minutes. Start cooling. Premix KCl with water and add into the batch at 100-110° F. Add Glydant at 100° F. Adjust pH if necessary. Homogenize if necessary.

Physical Properties: pH 4.0-4.5; viscosity: 3,000-4,000 cps

Example 34

Cream Conditioner for Permanent Waved Hair

| Ingredients: | % Wt. |
|---|---|
| Ammonyx ® 4 | 5.00 |
| Bio-PDO ™ (DuPont) | 1.50 |
| Panthenol | 0.50 |
| Citric Acid | q.s. |
| D.I. Water | q.s. to 100 |
| Stepan ® Cetyl Alcohol, NF | 2.50 |
| PPG-Ceteth 20 | 1.25 |
| Stepan ® Stearyl Alcohol 97 | 0.75 |
| Fragrance, Dye & Preservative | q.s. |
| Total | 100.0 |

Procedure: Add ingredients and mix while heating to 75° C. Mix until well blended. Cool with mixing to 30° C. and add fragrance, preservative, and dye if desired. Adjust pH with citric acid to 3-5.

Physical Properties: Opaque, white liquid; 2000 cps

Example 35

Clear Hair Conditioner

| Ingredients: | % Wt. |
|---|---|
| Ammonyx ® KP | 3.00 |
| Ammonyx ® CETAC | 1.50 |
| Bio-PDO ™ (DuPont) | 1.50 |
| Hydroxyethylcellulose | 0.90 |
| Polyquaternium 10 | 0.25 |
| Fragrance, Dye & Preservative | q.s. |
| Citric Acid | q.s. |
| D.I. Water | q.s. to 100 |
| Total | 100.0 |

Procedure: Disperse hydroxyethylcellulose in D.I. water with mixing until clear. Add Ammonyx® KP and mix until homogeneous. Slowly add Ammonyx® CETAC and mix until homogeneous. Disperse Polyquaternium-10 in Bio-PDO™ and add to above solution with mixing until clear. Adjust pH to 5.5, if necessary, with citric acid. Add fragrance, dye and preservative, if desired.

Physical Properties: pH 5.5; viscosity: 750 cps

Example 36

Spray-On Detangling Conditioner

| Ingredients: | % Wt. |
|---|---|
| D.I. Water | q.s. to 100.0 |
| Bio-PDO ™ (DuPont) | 1.50 |
| Ammonyx ® KP | 1.00 |
| Surfactant 193 (Dow Corning) Dimethicone Copolyol | 1.00 |
| Tween ® 20 (ICI) Polysorbate-20 | 0.30 |
| Citric Acid (50%) | q.s. |
| Fragrance, Dye & Preservative | q.s. |
| Total | 100.0 |

Procedure: Into a vessel equipped with agitation, add first four ingredients. Mix well. Premix fragrance and Tween® 20 in a separate container. Add to the batch. Mix well. Adjust pH with citric acid, if necessary. Add dye and preservative as desired.

Physical Properties: pH 4.0-4.4; Viscosity at 25° C.: water thin

Example 37

Moisturizing Spray

| Ingredients: | % Wt. |
|---|---|
| Water | 70.8 |
| Preservative | 0.2 |
| Bio-PDO ™ (DuPont) | 28.0 |
| Ammonyx® GA-70PG | 0.9 |
| Hydrolyzed Silk | 0.1 |
| Fragrance | 0.1 |
| Total | 100.0 |

Procedure: Charge water. Add Bio-PDO™. Heat to 50° C. and blend in Ammonyx® GA-70PG. Mix well until homogeneous. Cool with mixing. At 30° C., add propyl paraben and hydrolyzed silk. Cool to 25° C., add fragrance. Adjust pH to 5.5-6.5 with citric acid or sodium hydroxide.

Physical Properties: Viscosity: 20 cps

Example 38

Men's After Shave

Clear Microemulsion

| Ingredients: | % Wt. |
|---|---|
| Phase 1 | |
| Stepan ® PEG 400 MO | 12.7 |
| Stepan ® IPM | 11.0 |
| Stepan ® PEG 400 ML | 7.0 |
| Bio-PDO ™ (DuPont) | 3.5 |
| Stepan ® GMO | 3.0 |
| DC 556 Silicone Fluid (Dow Corning) | 1.0 |
| Phase 2 | |
| Ethanol | 25.0 |
| Triethanolamine | q.s. |
| Fragrance, dye, preservative | q.s. |
| D.I. Water | q.s. to 100 |
| Total | 100.0 |

Procedure: Heat D.I. water to 95° C. Mix the components of Phase (1) and heat to 95° C. Add Phase (1) to D.I. water with mixing. Cool to 30° C., and add ethanol. Adjust pH to 7.0-8.0 with triethanolamine. Add fragrance, dye, and preservative, if desired. This formula will create a clear microemulsion.

Physical Properties: pH 7.0-8.0; viscosity: 40 cps

Example 39

Foundation

| # | SEQ. | INGREDIENT | NMN2-43-1 | NMN2-43-2 | NMN2-43-3 |
|---|---|---|---|---|---|
| 1 | A | Deionized Water | 63.00 | 63.00 | 63.00 |
| 2 | A | CMC 7H3SF | 0.30 | 0.30 | 0.30 |
| 3 | A | Veegum Ultra Granules | 0.35 | 0.35 | 0.35 |
| 4 | A | Alcolec S (Lecithin) | 0.40 | 0.40 | 0.40 |
| 5 | A | Triethanolamine 99% | 1.25 | 1.25 | 1.25 |
| 6 | A | Propylene Glycol | 6.00 | — | — |
| 7 | A | Butylene Glycol | — | 6.00 | — |
| 8 | A | Bio-PDO ™ (1,3-Propanediol) | — | — | 6.00 |
| 9 | B | Titanium Dioxide (water dispersible) | 8.00 | 8.00 | 8.00 |
| 10 | B | Red Iron Oxide | 0.40 | 0.40 | 0.40 |
| 11 | B | Yellow Iron Oxide | 0.80 | 0.80 | 0.80 |
| 12 | B | Black Iron Oxide | 0.10 | 0.10 | 0.10 |
| 13 | B | Colloidal Kaolin | 2.00 | 2.00 | 2.00 |
| 14 | B | Methyl Paraben | 0.20 | 0.20 | 0.20 |
| 15 | C | Permethyl ® 102A (Isoeicosane) | 10.00 | 10.00 | 10.00 |
| 16 | C | Isostearic Acid | 1.00 | 1.00 | 1.00 |
| 17 | C | Stearic Acid Triple Pressed | 2.50 | 2.50 | 2.50 |
| 18 | C | LIPO GMS 450 (Glyceryl Monostearate) | 1.50 | 1.50 | 1.50 |
| 19 | C | Liponate TDTM (Tridecyl Trimelitate) | 1.00 | 1.00 | 1.00 |
| 20 | C | LIPO GMS 470 (Glyceryl Monostearate) | 1.00 | 1.00 | 1.00 |
| 21 | C | Propyl Paraben | 0.20 | 0.20 | 0.20 |
| | | FORMULA TOTALS | 100.00 | 100.00 | 100.00 |

The manufacturing procedure for this emulsion was typical for all oil-in-water type products. Sequence A was dispersed and when the gums were completely hydrated and the phase was uniform, pre-ground Sequence B (pigment phase) was added to it and mixed until both phases were completely uniform and homogeneous. Sequence C was weighed in a separate vessel and heated to 75°-80° C. until all the solids were melted and the phase was uniform. Sequence A was then heated to 75°-80° C. When all the phases were all at the proper temperatures, Sequence C (oil phase) was slowly added to Sequences A & B (water phase). The emulsion was allowed to mix at 75° C. for 15 minutes and then cooled to 25° C. Samples for testing were then poured off and placed at their respective stability stations in preparation for the 4 week study. The color and powder fill loading in these formulations was kept constant at 11.30% dry pigment. Conventional powder fill ingredients were chosen for these formulations as to eliminate any potential variability in test results.

Physical Testing:

| | Brookfield Model RV - Spindle 5 at 20 rpm for 1 minute (factor × 200) | | | | | | | |
|---|---|---|---|---|---|---|---|---|
| | Initial pH | Initial Viscosity | 1 Week Viscosity | 2 Week pH | 2 Week Viscosity | 3 Week Viscosity | 4 Week pH | 4 Week Viscosity |
| NMN2-43-1 | 7.95 | 2900 | 3100 | 8.02 | 3100 | 3100 | 7.99 | 3100 |
| NMN2-43-2 | 8.03 | 2900 | 3100 | 8.00 | 3200 | 3300 | 8.04 | 3200 |
| NMN2-43-3 | 8.03 | 2400 | 2900 | 7.94 | 2900 | 2900 | 8.02 | 2900 |

Viscosity readings throughout the 4 week test period showed that there was no unusual build or decrease in viscosity. Oven stability consisted of R/T, 45° C., and 2 Freeze/Thaw cycles. After 4 weeks, samples showed no signs of separation, sweating, severe loss of viscosity, change in consistency, loss of structure, odor problems, or color change at any temperature.

Aesthetic Properties:

All samples were evaluated for potential differences in odor, color, appearance, application, texture, feel, wearability, or any other differences, if any. All foundation samples were evaluated side-by side. In no cases were there any perceivable differences in any of the aesthetic properties associated with these types of cosmetic properties. Any differences noticed were insignificant and were not a result of the ingredient changes. These were all fragrance free formulations, and there were no apparent odor differences in any of the samples.

Example 40

Mascara

| # | SEQ. | INGREDIENT | NMN2-44-1 | NMN2-44-2 | NMN2-44-3 |
|---|---|---|---|---|---|
| 1 | A | Deionized Water | 49.00 | 49.00 | 49.00 |
| 2 | A | Xanthan Gum | 0.15 | 0.15 | 0.15 |
| 3 | A | Veegum HV Granules | 0.55 | 0.55 | 0.55 |
| 4 | A | Disodium EDTA | 0.05 | 0.05 | 0.05 |
| 5 | A | Triethanolamine 99% | 0.50 | 0.50 | 0.50 |
| 6 | A | Alcolec S (Lecithin) | 0.20 | 0.20 | 0.20 |
| 7 | A | Methyl Paraben | 0.30 | 0.30 | 0.30 |
| 8 | A | Propylene Glycol | 10.00 | — | — |
| 9 | A | Butylene Glycol | — | 10.00 | — |
| 10 | A | Bio-PDO ™ (1,3-Propanediol) | — | — | 10.00 |
| 11 | B | Black Iron Oxide | 9.00 | 9.00 | 9.00 |
| 12 | C | DC 345 Fluid (D5 Cyclomethicone) | 4.50 | 4.50 | 4.50 |
| 13 | C | DC5225C Formulation Aid | 0.90 | 0.90 | 0.90 |
| 14 | C | White Beeswax | 7.25 | 7.25 | 7.25 |
| 15 | C | Carnauba Wax #1 | 3.50 | 3.50 | 3.50 |
| 16 | C | Stearic Acid Triple Pressed | 1.80 | 1.80 | 1.80 |
| 17 | C | Lipomulse 165 (Glyceryl Monostearate) | 1.80 | 1.80 | 1.80 |
| 18 | C | Indopol H100 (Polybutene) | 3.50 | 3.50 | 3.50 |
| 19 | C | Phenoxyethanol | 1.00 | 1.00 | 1.00 |

-continued

| # | SEQ. | INGREDIENT | NMN2-44-1 | NMN2-44-2 | NMN2-44-3 |
|---|---|---|---|---|---|
| 20 | C | Propyl Paraben | 0.20 | 0.20 | 0.20 |
| 21 | C | PVP/Eicosene Colpolymer | 4.00 | 4.00 | 4.00 |
| 22 | C | Lipocol S (Stearyl Alcohol) | 1.80 | 1.80 | 1.80 |
|   |   | FORMULA TOTALS | 100.00 | 100.00 | 100.00 |

The manufacturing procedure for this formula was similar to that of the foundation in Example 24. Higher temperatures were required for the oil phase due to the high level of hard waxes employed in this product. Sequence A was dispersed and when the gums were completely hydrated and the phase was uniform, pre-ground sequence B (pigment phase) was added to it and mixed until both phases were completely uniform and homogeneous. Sequence C was weighed in a separate vessel and heated to 80°-85° C. until all the solids were melted and the phase was uniform. Sequence A was then heated to 75°-80° C. When all the phases were all at the proper temperatures, Sequence C (oil phase) was slowly added to Sequences A & B (water phase). The emulsion was allowed to mix at 75° C. for 15 minutes. When the batch began to thicken at around 45° C., a paddle mixer was used to adequately turn over and mix the batch. The batch was mixed and cooled to 35° C. Samples for testing were then poured off and placed at their respective stability stations in preparation for the 4 week study. The color loading in these formulations was kept constant at 9.00% dry pigment. No other powder fill, except for the black iron oxide pigment, was employed in these formulations. Additional powder fills will lend to a whitening and ashyness, which, in mascaras, is unacceptable.

Physical Testing:

| | Brookfield Model RV - Spindle T at 5 rpm for 1 minute (factor × 10,000) | | | | | | | |
|---|---|---|---|---|---|---|---|---|
| | Initial pH | Initial Viscosity | 1 Week Viscosity | 2 Week pH | 2 Week Viscosity | 3 Week Viscosity | 4 Week pH | 4 Week Viscosity |
| NMN2-44-1 | 8.78 | 140,000 | 300,000 | 8.76 | 340,000 | 360,000 | 8.75 | 380,000 |
| NMN2-44-2 | 8.48 | 190,000 | 370,000 | 8.43 | 420,000 | 450,000 | 8.45 | 420,000 |
| NMN2-44-3 | 8.58 | 180,000 | 320,000 | 8.55 | 380,000 | 430,000 | 8.55 | 420,000 |

Viscosity readings throughout the 4 week test period showed that there was no unusual build or decrease in viscosity. The variations seen are very typical for a product of this type and fall within an acceptable range for a mascara type product. Oven stability consisted of R/T, 45° C., and 2 Freeze/Thaw cycles. After 4 weeks, samples showed no signs of separation, sweating, severe loss of viscosity, change in consistency, loss of structure, odor problems, or color change at any temperature.

Aesthetic Properties:

All samples were evaluated for potential differences in odor, color, appearance, application, texture, feel, wearability, or any other differences, if any. All mascara samples were evaluated side-by side. In no cases were there any perceivable differences in any of the aesthetic properties associated with these types of cosmetic properties. Any differences noticed were insignificant and were not a result of the ingredient changes. Additionally, the mascara samples showed no differences in water resistance. Even though the mascara was not specifically designed to be water resistant, side by side, the products performed equally. These were all fragrance free formulations, and there were no apparent odor differences in any of the samples.

Example 41

Body Wash

| Ingredients: | % Wt. |
|---|---|
| Water | 45.0 |
| Ammonium Lauryl Sulfate, 25% | 21.0 |
| Ammonium Laureth Sulfate, 28% | 21.0 |
| Cocamidopropyl Betaine, 35% | 4.0 |
| Acrylates Copolymer, Structure 3001 (30%) | 5.0 |
| 1,3-Propanediol | 1.0 |
| Glycerin | 1.0 |
| PEG 10 Sunflower Glycerides | 0.5 |
| Soybean Oil | 0.2 |
| Fragrance | (0.2) |
| Cocamide MEA | 0.2 |
| PEG 5 Cocamide | 0.2 |

-continued

| Ingredients: | % Wt. |
|---|---|
| Guar Hydroxypropyl trimonium Chloride | 0.2 |
| Diisopropanolamine | 0.1 |
| Methylcellulose | 0.05 |
| Carbomer | 0.05 |
| Tetrasodium EDTA | 0.05 |
| Methylchloroisothiazolinone, Methylisothiazolinone | 0.05 |
| Etidronic Acid | 0.05 |
| Guanine (CI 75170) | 0.05 |
| Mica (CI 77019) | 0.05 |
| Titanium Dioxide (CI 77891) | 0.05 |
| TOTAL | 100 |

Ingredients were combined in the following order, with propeller mixer agitation, allowing each ingredient to dissolve, disperse completely before adding the next. Batch was processed at 60° C.: Water, Acrylates polymer, ALS, ALES, GAB, Guar Hydroxypropyl trimonium Chloride, EDTA, PEG 10 Sunflower glycerides, soybean oil, cocamide MEA, PEG 5 cocamide, diisopropanolamine/methylcellulose/carbomer/guanine, mica/titanium oxide, glycerin.

Example 42

Baby Lotion

| Ingredients: | % Wt. |
| --- | --- |
| Water | 85.2 |
| 1,3-Propanediol | 3.0 |
| Myristyl Myristate | 2.5 |
| Glyceryl Stearate | 1.5 |
| Oleic Acid | 1.2 |
| Stearic Acid | 1.2 |
| Polysorbate 61 | 0.6 |
| C12-15 Alkyl Benzoate | 0.5 |
| Dimethicone | 0.5 |
| Isopropyl Palmitate | 0.5 |
| Sorbitan Stearate | 0.5 |
| Cetyl Alcohol | 0.5 |
| Synthetic Beeswax | 0.5 |
| Stearyl Alcohol | 0.5 |
| Benzyl Alcohol | 0.4 |
| Carbomer 934 | 0.4 |
| Fragrance | 0.1 |
| Methylparaben | 0.2 |
| Propylparaben | 0.05 |
| Butylparaben | 0.05 |
| BHT | 0.05 |
| D&C Red 3 | trace |
| TOTAL | 100 |

Ingredients were combined in the following order, allowing each to dissolve/disperse completely before adding the next:

Phase A: Disperse Carbomer in water with high speed agitation, allowing particles to wet completely. Add 1,3-propanediol. Heat to 70° C.

Phase B: Combine Myristyl Myristate, glyceryl stearate, Oleic Acid, Polysorbate 61, C12-15 Alkyl Benzoate, Dimethicone, Isopropyl Palmitate, Sorbitan Stearate, Cetyl Alcohol, Synthetic Beeswax, Stearyl; Alcohol, Benzyl Alcohol, Methylparaben, Propylparaben, Butylparaben, and BHT, heat to 70° C.

With continuous high speed agitation, slowly add Phase B to Phase A to form emulsion. Remove from heat and begin cooling with continued agitation. After several minutes of mixing, add NaOH, dissolved in a small amount of water. Batch will thicken. When Batch reaches room temperature, add color, fragrance, and replace water lost to evaporation. Batch is complete.

Example 43

Sulfate-Free Shampoo

| Phase | Ingredients: | % Wt. |
| --- | --- | --- |
| A | Water | 33.82 |
| A | NA2EDTA | 0.05 |
| A | BIOTERGE AS 40 | 45.00 |
| A | GLUCAMATE DOE 120 | 1.50 |
| A | 1,3-PROPANEDIOL | 4.75 |
| B | MONAMID CMA | 3.00 |
| B | VELVETEX BK 35 | 10.00 |
| C | KATHON CG | 0.06 |
| C | MACKPEARL 140V | 1.50 |
| D | CITRIC ACID, 20% SOLN TO PH 6.0-6.5 | 0.32 |
| | TOTAL | 100.00 |

Manufacturing Process:

Phase A: Combine Phase A ingredients into water and heat with mixing to 75° C. Slowly add remaining Phase A ingredients. Hold temperature at 75° C. and mix slowly.

Phase B: Combine phase B ingredients and heat to 75° C. with slow mixing. Add Phase B to Phase A and mix until uniform.

Phase C: Add Phase C one at a time

Phase D: Use Phase D to adjust the pH of batch to 6.0-6.5

Example 44

Liquid Powder

Using the present invention liquid powder can be prepared using bio-based propanediol caprylate. Obtain the ingredients in the proportionate amounts listing in Table 1. Starting with the ingredients in Table 1, phase A, add inulin lauryl carbamate to water and disperse CARBOPOL ULTREZ 10 (B.F. Goodrich Company, New York, N.Y.). Blend the mixture of phase A ingredients for about 10 minutes, until the carbomer is completely dispersed and hydrated. Under light agitation raise the temperature of the mixture to about 70° C.

In a separate clean container, combine the components listed in Table 1, phase B in the amount stipulated by the table, including bio-based propanediol caprylate, and heat to about 75° C. After the components have been fully combined and are at the target temperature, slowly add phase B mixture to the phase A mixture. Apply rapid agitation and hold temperature between about 70° C. and about 75° C. for 30 minutes. After 30 minutes allow the combined mixtures to cool to 55° C. and with continuous agitation slowly add corn starch of phase C in the amount stipulated by Table 1. When the corn starch has been thoroughly mixed into the combined ingredients of phases A and B, add fragrance and preservative of phase C. Adjust the fragrance and preservative as desired. Measure the pH and then if necessary adjust the pH to between about 5.5 to about 6.0 with triethanolamine. When the pH has been adjusted, cool to room temperature.

TABLE 1

| Ingredients: | % WT. |
| --- | --- |
| Phase A | |
| Water | 55.7 |
| Inulin lauryl carbamate | 0.5 |
| Carbopol Ultrez 10 (Carbomer) | 0.3 |
| Phase B | |
| Neopentyl glycol diheptanoate and isodecane | 5.0 |
| Stearamidopropyl morpholine lactate (25%) | 2.0 |
| Stearyl benzoate | 3.0 |
| Sorbitan oleate | 0.5 |
| Bio-based propanediol caprylate | 0.5 |

TABLE 1-continued

| Ingredients: | % WT. |
|---|---|
| Phase C | |
| Topical Starch (Corn Products corn starch 037570) | 30.0 |
| Fragrance | q.s. |
| Phenoxyethanol and DMDM hydantoin | q.s. |
| Paragon III (Methylparaben and propylparaben) | q.s. |
| Triethanolamine (99%) | q.s. to pH 5.5-6.0 |

Example 45

Pearlized Milk Bath

The present invention can be used to prepare a pearlized milk bath using bio-based propanediol distearate. Following the percentages in Table 2, combine UCARE polymer LR-400 with a sufficient amount water to hydrate. Then following the percentage listed in Table 2, blend in PLANTOPON 611 L (Fitz Chem Corporation, Itasca, Ill.) and LAMESOFT PO 65 (Fitz Chem Corporation, Itasca, Ill.) until the mixture reaches uniform consistency.

At this point add polymer solution in the amount listed in Table 2 to the mixture and agitate until uniform consistency is restored. Next following the percentage listed in Table X, add glycerin, STANDAMOX CAW (Fitz Chem Corporation, Itasca, Ill.), NUTRILAN MILK (Fitz Chem Corporation, Itasca, Ill.), bio-based propanediol distearate and mix well until the mixture is again of uniform consistency. Measure the pH and if necessary adjust with citric acid to reach a final pH of between about 6 to about 7. Finally add preservative, dye, fragrance and enough water to reach the desired volume. The final viscosity of the mixture should be between about 5,000 cPs to about 10,000 cPs.

TABLE 2

| Ingredients: | % WT. |
|---|---|
| Plantopon 611 L (Sodium laureth sulfate and lauryl glucosidee and cocamidopropyl betaine) | 22.00 |
| Lamesoft PO 65 (Coco glucoside and glyceryl oleate) | 3.00 |
| Standamox CAW (Cocamidopropylamine oxide) | 3.00 |
| Bio-based propanediol distearate | 2.00 |
| Nutrilan Milk (Hydrolyzed milk protein) | 1.50 |
| Emery 917 (Glycerin) | 0.50 |
| Ucare polymer LR-400 (Amerchol) (polyquaterium-10) | 0.10 |
| Water, preservative, fragrance, dye | q.s. |

Example 46

Gentle Baby Shampoo

The present invention can be use in the preparation of a gentle baby shampoo using bio-based propanediol oleate. Obtain the ingredients in the proportionate amounts listed in Table 3. Heat an amount water of slight less than required volume according to Table 3, to about 40° C. Add ingredients in the amount and order listed in Table 3. Mix the ingredients together with gentle agitation, do not exceed 100 rpm. When the mixture has reached uniform consistency, add water to bring the mixture to the desired final volume. The let the mixture cool to room temperature. The resulting shampoo is prepared correctly should appear clear and colorless.

TABLE 3

| Ingredients: | % WT. |
|---|---|
| Deionized water | q.s. to 100 |
| Tego Betaine L-7 (cocamidopropyl betaine) | 18.5 |
| Neosorb 70/20 (sorbitol) | 16.9 |
| Plantaren 1200 UP (lauryl glucoside) | 15.9 |
| Plantaren 818 UP (coco glucoside) | 12.5 |
| Amisoft LS-11 (sodium lauroyl glutamate) | 5.0 |
| Bio-based propanediol oleate | 2.2 |
| D-panthenol USP (D-panthenol) | 1.0 |
| Sensomer CI-50 (Ondeo Nalco (hydroxypropyltrimonium chloride) | 0.5 |
| Crotein HKP Powder (keratin amino acid) | 0.4 |
| Fragrance | 0.1 |
| Preservative | q.s. |

Example 47

Moisturizing Body Wash

The present application can be used in the preparation of a moisturizing body wash using bio-based propanediol stearate. To prepare such a moisturizing body wash, start by obtaining the list of ingredients in the proportional amounts listing in Table 4. Mix the together the sodium laureth sulfate, JORDAPON CI (BASF Corporation, Mount Olive, N.J.), AVANEL S150 CGN (BASF Corporation, Mount Olive, N.J.), PEG-150 distearate, Cocamidopropyl betaine, Cocamide MEA, and bio-based propanediol stearate in approximately half of the total water required for the desired volume. After these ingredients thoroughly combined, apply heat to raise the temperature of the mixture to about 65° C. Maintain a temperature of about 65° C. until all components have dissolved and a uniform mixture is obtained. While allowing the mixture to cool, add LUVIQUAT PQ 11 (BASF Corporation, Mount Olive, N.J.) and gently agitate.

In a separate container, mix the CREMOPHOR PS20 (BASF Corporation, Mount Olive, N.J.), vitamin E acetate and fragrance together until fully blended. When the temperature of the first mixture has dropped to below 40° C., add the mixed the CREMOPHOR PS20 (BASF Corporation, Mount Olive, N.J.), vitamin E acetate and fragrance to the mixture. Next added the D,L-PANTHENOL 50 W (BASF Corporation, Mount Olive, N.J.) to the mixture and gently agitate until thoroughly blended. Next add the D,L-Panthenol 50 W to the mixture and gently agitate until thoroughly blended. Next add the disodium EDTA to the mixture and gently agitate until thoroughly blended. Next, add to the mixture a preservative, selected to be adequate for the expected conditions and shelf-life. Finally, add water to bring the mixture to the desired volume, and agitate until an even consistency is achieved.

TABLE 4

| Ingredients: | % WT. |
|---|---|
| Deionized water | 59.1 |
| Sodium laureth sulfate | 10.0 |
| JORDAPON CI (sodium cocoyl isethionate) | 10.0 |
| AVANEL S150 CGN (sodium C12-15 pareth sulphonate) | 3.0 |
| PEG-150 distearate | 0.5 |
| Cocamidopropyl betaine | 8.0 |
| Cocamide MEA | 3.0 |
| Bio-based propanediol stearate | 2.0 |
| LUVIQUAT PQ11 (polyquaternium-11) | 1.0 |
| CREMOPHOR PS20 (polysorbate-20) | 2.0 |
| D,L-PANTHENOL 50 W (panthenol) | 0.5 |
| Vitamin E acetate | 0.1 |
| Fragrance | 0.2 |

Example 48

Deep Penetrating Hair Reconstructor

The present invention can be used in the preparation of a deep penetrating hair reconstructor using bio-based propanediol dicaprylate. To prepare such a hair reconstructor obtain the ingredients as listed in and in the relative quantities as depicted in Table 5. Then, mix the DEHYQUART L 80 (Cognis GMBH, Dusseldorf, Del.) CETIOL CC (Cognis GMBH, Dusseldorf, DE), DC 949 (Dow Corning, Midland Mich.), GLUADIN WLM (Cognis GMBH, Dusseldorf, DE), perfume, and preservative, i.e. all the components of table 5, phase A. Agitate the component of phase A until completely homogeneous.

In a separate container, disperse the LAMESOFT PW 45 (Grunau Illertissen GmbH, Illertissen, DE) in a quantity of water as shown in Table 5, phase B. When LAMESOFT PW 45 has been fully dispersed add it to the phase A mixture.

In a separate container, mix the bio-based propanediol dicaprylate in deionized water in a quantity of water as shown in Table 5, phase C until a homogeneous cream is obtained. Then, add phase A and B to phase C and agitate until a desire consistency is achieved. If necessary adjust pH to between about 6.5 and about 7.5 using either citric acid or sodium hydroxide.

| Ingredients: | % WT. |
|---|---|
| Phase A | |
| DEHYQUART L 80 (Dicocoylethyl hydroxyethylmonium methosulfate and propylene glycol) | 2.00 |
| CETIOL CC (Dicaprylyl carbonate) | 1.00 |
| DC 949 (Dow Corning) (Amodimethicone and cetrimonium chloride and trideceth-12) | 1.00 |
| GLUADIN WLM (Hydrolized wheat protein) | 2.00 |
| Perfume | q.s. |
| Preservative | q.s. |
| Phase B | |
| LAMESOFT PW 45 (Cetyl palmitate and beheneth-10 and hydrogenated castor oil and glyceryl stearate) | 4.00 |
| Water | 37.75 |
| Phase C | |
| Bio-based propanediol dicaprylate | 2.25 |
| Water | 50.00 |

Example 49

Bronzing Stick

The present invention can be used to prepare a bronzing stick using both bio-based propandiol myristate and bio-based propanediol diprylate. To prepare such a bronzing stick, obtain all the ingredients in the proportions indicated in Table 6. Combine PEG-8, tocopherol, ascorbyl palmitate, ascorbic acid and citric acid, i.e. all the ingredients of Table 6, Phase C and mix together until homogenized. Combine the ingredients of Phase C, with the microcrystalline wax SP-1028 (Strahl & Pitsch, Inc., West Babylon, N.Y.), lauryl laurate (Strahl & Pitsch, Inc., West Babylon, N.Y.), microcrystalline wax SP-89 (Strahl & Pitsch Inc., West Babylon, N.Y.), microcrystalline wax SP-19 (Strahl & Pitsch Inc., West Babylon, N.Y.), caprylic/capric triglycerides (Cognis GMBH, Dusseldorf, DE), bio-based propandiol myristate, bio-based propanediol diprylate, Trioctyldodecyl citrate (Phoenix, Merseyside, UK), and Propylparaben (Spectrum Chemical Manufacturing Corporation, Gardena, Calif.). Mix the combination while heating. Bring the combination to about 85° C. under continuous agitate. Maintain 85° C. until the mixture has reached homogeny.

In a separate container, mix together the Colorona bronze cosmetic pigment (Rona Cosmetics GmBH, Darmstadt DE), Timiron MP-10 cosmetic pigment (Rona Cosmetics GmBH, Darmstadt DE), Colorona copper cosmetic pigment (Rona Cosmetics GmBH, Darmstadt DE), and Biron LF-2000 cosmetic pigment (Rona Cosmetics GmBH, Darmstadt DE), i.e. all the components of Table 6, phase B. When the phase B components have been thoroughly mixed, blend them into the already combined phase A and phase C mixture, while continuing to heat at 85° C. After the phase B mixture has been thoroughly combined with phase A and phase C and homogeny has reached, allow the mixture to cool to between about 70° C. and about 80° C. While the mixture is between about 70° C. and about 80° C., pour the mixture into molds to create sticks. Allow the mixture to fully cool to room temperature before removing the formed sticks from the molds.

TABLE 6

| Ingredients: | % WT. |
|---|---|
| Phase A | |
| Microcrystalline wax SP-1028 (Strahl & Pitsch) | 11.70 |
| Lauryl laurate (Strahl & Pitsch) | 3.00 |
| Microcrystalline wax SP-89 (Strahl & Pitsch) | 2.80 |
| Microcrystalline wax SP-19 (Strahl & Pitsch) | 2.80 |
| Caprylic/capric triglycerides (Cognis) | 14.00 |
| Bio-based propanediol myristate | 15.00 |
| Bio-based propanediol diprylate | 19.40 |
| Trioctyldodecyl citrate (Phoenix) | 3.00 |
| Propylparaben (Spectrum Chemical) | 0.20 |
| Phase B | |
| Colorona bronze cosmetic pigment (Mica and iron oxides) | 13.00 |
| Timiron MP-10 cosmetic pigment (Mica and titanium oxides) | 3.00 |
| Colorona copper cosmetic pigment (Mica and iron oxides) | 3.00 |
| Biron LF-2000 cosmetic pigment (Bismuth oxychloride) | 3.00 |
| Phase C | |
| PEG-8 | 0.02 |
| tocopherols | 0.02 |
| ascorbyl palmitate | 0.02 |
| ascorbic acid | 0.02 |
| citric acid | 0.02 |

Example 50

Lip Gloss

Mix caster oil, Bio-PDO™ distearate, cetyl alcohol and heat the mixture to 75° C. until a uniform solution is formed. Add color pigment and heat the mixture while stirring till no lumps are remained. Add TiO2 and heat to 85° C. with stirring until a uniform product is formed. Add fragrance while cooling and transfer into containers.

| Ingredients: | % WT. |
|---|---|
| Phase A | |
| Caster oil | 55.0 |
| Bio-PDO ™ distearate | 16.0 |
| Cetyl alcohol [1] | 1.6 |
| Pigment (iron oxide) [2] | 1.5 |
| TiO2 | 25.4 |
| Fragrance | QS |

[1] The Chemistry Store.com, Cayce, SC
[2] Somerset Cosmetic Co. LLC, Renton, WA

Example 51

Pearlized Milk Bath

Poly(diallyldimethylammonium chloride), 20 wt % in water was blended with PLANTOPON 611 L, polyglucoside, Bio-PDO™ oleate and cocamide DMA in the proportional amounts listed in Table until the mixture reaches uniform consistency. Then glycerin, milk protein, Bio-PDO™ oleate, Bio-PDO™ distearate were added and mixed well until the mixture is again of uniform consistency. Measure the pH and if necessary adjust with citric acid to reach a final pH of between about 6 to about 7. Finally add preservative, dye, fragrance and enough water to reach the desired volume. The final viscosity of the mixture should be between about 5,000 cPs to about 10,000 cPs.

| Ingredients: | % WT. |
|---|---|
| Plantopon 611 L [3] | 22.00 |
| Polyglucose (decyl glucoside) [2] | 3.00 |
| Cocamide DMA [1] | 3.00 |
| Bio-PDO ™ oleate | 0.50 |
| Bio-PDO ™ distearate | 2.00 |
| Milk protein | 1.50 |
| Glycerin | 0.50 |
| Poly (diallyldimethylammonium chloride), (20 wt % in water) [4] | 1.00 |
| Water, preservative, fragrance, dye | q.s. |

[1] The Chemistry Store.com, Cayce, SC
[2] Somerset Cosmetic Co. LLC, Renton, WA
[3] Fitz Chem Corporation, Itasca, IL
[4] Sigma-Aldrich, Milwaukee, WI

Example 52

Moisturizing Body Wash

Mix the together the blend 213 (Chemistry Store), Cocamidopropyl betaine, Cocamide DEA, and Bio-PDO™ distearate. After these ingredients thoroughly combined, apply heat to raise the temperature of the mixture to about 70° C. Maintain a temperature of about 70° C. until all components have dissolved and a uniform mixture is obtained. While allowing the mixture to cool, add poly(diallyldimethylammonium chloride) solution and gently agitate.

When the temperature of the first mixture has dropped to below 40° C., add the polysorbate-60, vitamin E acetate to the mixture. Next added the Panthenol to the mixture and gently agitate until thoroughly blended. Next add the disodium EDTA to the mixture and gently agitate until thoroughly blended. Next, add to the mixture a preservative, fragrance and water to bring the mixture to the desired volume, and agitate until an even consistency is achieved.

| Ingredients: | % WT. |
|---|---|
| Blend 213 [1] | 47.0 |
| Sodium Laureth Sulfate | |
| Cocamidopropyl Betaine | |
| Cocamide DEA | |
| PEG-150 Distearate | |
| Cocamidopropyl Betaine [1] | 4.0 |
| Cocamide DEA [1] | 3.0 |
| Bio-PDO ™ distearate | 2.0 |
| Poly (diallyldimethylammonium chloride), (20 wt % in water) [4] | 5.0 |
| Polysorbate-60 [2] | 2.0 |
| Panthenol | 0.5 |
| Vitamin E acetate | 0.1 |
| Disodium EDTA | 0.5 |
| Preservative | 0.5 |
| D.I Water, Fragrance | q.s. |

[1] The Chemistry Store.com, Cayce, SC
[2] Somerset Cosmetic Co. LLC, Renton, WA
[3] Fitz Chem Corporation, Itasca, IL
[4] Sigma-Aldrich, Milwaukee, WI

Example 53

Bronzing Stick

Mix the ingredients of Phase A. Heat the mixture to about 70° C. under continuous agitation. Maintain 70° C. until the mixture has reached homogeneous.

In a separate container, mix together the TiO2, and pigment(s) and blend them into the phase A mixture, while continuing to heat at 70° C. After the phase B mixture has been thoroughly combined with phase A and homogeny has reached, allow the mixture to cool to about 50° C., pour the mixture into molds to create sticks. Allow the mixture to fully cool to room temperature before removing the formed sticks from the molds.

| Ingredients: | % WT. |
|---|---|
| Phase A | |
| Emulsifyin Wax NF [1] | 17.42 |
| Bio-PDO ™ distearate | 18.13 |
| Bio-PDO ™ dilaurate | 14.10 |
| Bio-PDO ™ dicaprylate | 19.54 |
| Cetyl alcohol [1] | 2.27 |
| Germaben II [1] | 0.20 |
| PEG-8 | 0.02 |
| Citric acid | 0.12 |
| Phase B | |
| TiO2 | 25.18 |
| Pigment (Iron oxide) [2] | 3.02 |

[1] The Chemistry Store.com, Cayce, SC
[2] Somerset Cosmetic Co. LLC, Renton, WA

Example 54

Hand Cleanser

Blend ammonium laury sulfate, cocamide DEA, sodium lauryl sulfate solution and BioPDO™ at room temperature. Add BioPDO™ stearate and Irgsan. Heat to 60° C. while stirring until solids are dissolved. Cool to 30° C., add EDTA. Stir until a homogeneous solution is formed. Adjust to pH 6 with citric acid. Add fragrance.

| Ingredients: | % WT. |
|---|---|
| Ammonium Lauryl Sulfate (ALS) (28%) | 26.0 |
| Cocamide DEA [2] | 6.0 |
| Sodium Lauryl Sulfate (SLS) (25%) | 18.0 |
| Bio-PDO ™ [1] | 1.0 |
| Water | 44.5 |
| Bio-PDO ™ stearate | 0.5 |
| Irgasan [6] | 0.2 |
| Tetrasodium EDTA (5 wt %) | 2.0 |
| Citric acid (50 wt %) | QS |
| Fragrance | 0.2 |

[1] DuPont Tate & Lyle Bio Products
[2] The Chemistry Store.com, Cayce, SC
[3] Somerset Cosmetic Co. LLC, Renton, WA
[4] Stephan Co. Northfield, IL
[5] Noveon, Cleveland, OH
[6] Sigma-Aldrich, Milwaukee, WI

Example 55

Sunscreen

Combine components of phase A mix and heat to 75° C. In a separate container mix the components of phase B and heat to 75° C. Combine phase B with phase A. Cool it to 45° C. Add components of phase C. Mix it thoroughly. Add components of phase D and E. Mix it until viscosity developed.

| Ingredients: | % WT. |
|---|---|
| Phase A | |
| Deionized water | 58.01 |
| Carbopol 934 (Noveon, Cleveland, OH) | 0.40 |
| Disodium EDTA | 0.125 |
| Bio-PDO ™ | 4.00 |
| Phase B | |
| Oxybenzone [3] | 15.50 |
| Phenylethyl benzoate | 10.00 |
| Bio-PDO ™ stearate | 2.00 |
| Ceteareth [3] | 2.00 |
| Phase C | |
| Deionized water | 5.00 |
| TEA | 0.50 |
| Phase D | |
| Germaben II [2] | 1.65 |
| Bio-PDO ™ [1] | 0.50 |
| Phase E | |
| Idopropynyl butylcarbamate | 0.20 | pH: 7
Viscosity: 12700 @ 30 rpm
[1] DuPont Tate & Lyle Bio Products
[2] The Chemistry Store.com, Cayce, SC
[3] Somerset Cosmetic Co. LLC, Renton, WA
[4] Stephan Co. Northfield, IL
[5] Noveon, Cleveland, OH
[6] Sigma-Aldrich, Milwaukee, WI

Example 56

Liquid Automatic Dishwashing Detergent

| Ingredients | Wt. % |
|---|---|
| Water | 54.30 |
| Citric Acid | 5.93 |
| Bio-PDO ™ (DuPont) | 6.92 |
| Carbopol ™ 934 | 2.18 |
| NaOH (50%) | 5.74 |
| Sodium Bo rate | 0.99 |
| Sodium Citrate | 3.96 |
| Sodium Formate | 1.98 |
| CaCl | 0.10 |
| Sodium Xylene Sulfanate (40%) | 4.95 |
| EO/PO Block Copolymer | 1.98 |
| Sodium Polyacrylate Mn1200 (45%) | 9.89 |
| Protease | 0.69 |
| Amylase | 0.20 |
| Lemon Essential Oil | 0.20 |
| Total | 100.0 |

Procedure: Combine and stir $H_2O$, citric acid and Bio-PDO™. Add Carbopol™ to mixture and stir until dissolved. Slowly add NaOH, and thereafter add remaining ingredients.

Benefits: The resulting liquid dishwashing detergent displays very good stability, enhanced rheology effects and less environmental inpact.

Example 57

Liquid Laundry Detergent

| Ingredients | Wt. % |
|---|---|
| Linear Dodecyl Benzene Sulfonate | 6.93 |
| Coconut Fatty Acid (C12-C18) | 7.52 |
| Tergitol 15-S-7 | 16.83 |
| Triethanolamine | 7.52 |
| Bio-PDO ™ (DuPont) | 10.89 |
| Citric Acid (50%) | 6.33 |
| KOH (45%) | 9.30 |
| Water | 33.65 |
| Protease | 0.69 |
| Amylase | 0.20 |
| Lavendar Essential Oil | 0.10 |
| FD&C Blue 1 | 0.03 |
| FD&C Red 40 | 0.01 |
| Total | 100.0 |

Procedure: Combine Linear Dodecyl Benzene Sulfonate, $H_2O$, Triethanolamine and Bio-PDO™, and stir mixture at 70° C. Add Tergitol. Melt the fatty acids and add to the mix. Slowly add KOH, then slowly add the citric acid. Cool mixture below 30° C. Add the enzymes, fragrance and dye.

Benefits: The resulting liquid laundry detergent exhibits very good stability, excllelent cloud point and enhanced rheology effects.

Example 58

Liquid Laundry Detergent

| Ingredients | Wt. % |
|---|---|
| C12-C13 Linear Alcohol EO-7 | 4.0 |
| Linear Dodecyl Benzene Sulfonate (60%) | 14.0 |
| Sodium Laureth Sulfate (60%) | 5.0 |
| Sodium Citrate | 4.0 |
| Sodium Borate | 4.0 |
| Bio-PDO ™ (DuPont) | 3.0 |
| Tinopal CBS-X | 0.1 |
| Protease | 0.7 |
| Amylase | 0.2 |
| Monethanolamine | 0.5 |
| Coconut Fatty Acid (C12-C18) | 2.0 |
| Water | 62.5 |
| Total | 100.0 |

Physical Properties

| | |
|---|---|
| pH, as is | 8.5 |
| Soluble Solids, 5 by refractometer | 29.3 |
| Residue on Drying, % by weight | 28 |
| Viscosity, cPs @ 25° C. | 194 |
| Visual Viscosity | Water Thin |
| Freeze/Thaw Stability | −15°/25° C. |
| Heat Stability (50° C.) | 30 days |

Example 59

Hand Dishwashing Liquid

| Ingredients | Wt. % |
|---|---|
| Bio-PDO ™ (DuPont) | 15.35 |
| Linear Dodecyl Benzene Sulfonate | 19.95 |
| Triethanolamine | 6.14 |
| Cocamide DEA | 10.74 |
| Tergitol 15-S-7 | 4.60 |
| Sodium Laureth-3EO Sulfate (28%) | 4.60 |
| Coco Amido Propyl Betaine | 7.67 |
| Polyquaternium-6 (20%) | 3.07 |
| NaCl (25%) | 1.53 |
| Sodium Xylene Sulfonate (40%) | 6.55 |
| Water | 19.19 |
| Lemon Essential Oil | 0.58 |
| FD&C Yellow 5 | 0.03 |
| FD&C Red 40 | 0.01 |
| Total | 100.0 |

Procedure: Combine all liquid ingredients and stir mixture at 70° C. Gradually add Linear Dodecyl Benzene Sulfonate and stir until dissolved in mixture and mixture is clear. Cool mixture below 30° C. and add fragrance and coloring.

Benefits: The resulting hand dishwashing liquid exhibits very good stability, improved foaming, excellent cloud point and requires less salt to adjust viscosity.

Example 60

Hand Dishwashing Liquid

| Ingredients | Wt. % |
|---|---|
| Bio-PDO ™ (DuPont) | 15.56 |
| Linear Dodecyl Benzene Sulfonate | 20.23 |
| Triethanolamine | 6.22 |
| Cocamide DEA | 10.89 |
| Tergitol 15-S-7 | 4.67 |
| Sodium Lauryl Sulfate | 4.67 |
| Coco Amido Propyl Betaine | 7.78 |
| Polyquaternium-6 (20%) | 3.11 |
| NaCl (25%) | 3.11 |
| Sodium Xylene Sulfanate (40%) | 3.50 |
| Water | 19.45 |
| Lemon Essential Oil | 0.78 |
| FD&C Yellow 5 | 0.04 |
| Total | 100.0 |

Procedure: Combine all liquid ingredients and stir mixture at 70° C. Gradually add Sodium Lauryl Sulfate and stir until dissolved and liquid mixture is clear. Gradually add Linear Dodecyl Benzene Sulfonate and stir until dissolved and liquid mixture is clear. Cool mixture below 30° C. and add fragrance and coloring.

Example 61

Detergents Comprising Esters Formed from Biologically Derived 1,3-Propanediol

Fatty acid glycol ester (e.g., Monoethylene glycol distearate) 5.0-30.0%; Fatty acid alkanolamide (e.g., Coconut oil acid monoethanolamide) 2.0-20.0%; Surfactant (e.g., Sodium lauryl triglycol ether-sulfosuccinate or Coconut-alkyldimethylamine oxide) 0.1-10.0%; Sodium salt (e.g., Mono- or Di-valent) 0.1-3.0%; and water up to 100%.

Addition of a fatty acid glycol ester with a fatty acid alkanolamide and an ether-sulfate-free surfactant will yield a pearlescent dispersion having 1) excellent pearlescent effect, 2) good storage ability, and 3) low viscosity. This composition will form a pearlescent dispersion with good flow properties and low surfactant content.

Example 62

Liquid Detergent Comprising Esters Formed from Biologically Derived 1,3-Propanediol Fatty acid glycol ester (e.g., Monoethylene glycol distearate) 5.0-30.0%; Fatty acid alkanolamide (e.g., Cocomonoethanolamide) 2.0-20.0%; Nonionic surfactant (e.g., $C_{10}$-$C_{12}$-Fatty polyol alkyl ester) 0.1-10.0%; water up to 100%.

Addition of a fatty acid glycol ester with a fatty acid alkanolamide and a nonionic surfactant will yield a pearlescent dispersion having 1) excellent pearl luster effect, 2) long shelf life, 3) compatibility with cationic surfactants, 4) resistance to hydrolysis, 5) low viscosity, and 6) reduced foaming.

Example 63

Liquid Detergent Comprising Esters Formed from Biologically Derived 1,3-Propanediol Fatty acid glycol ester (e.g., Ethylene glycol distearate) 5.0-40.0%; Nonionic surfactant (e.g., Laureth-7) 3.0-30.0%; Amphoteric surfactant (e.g., Cocoamidopropyl betaine and Cocoamphoacetate) 0.0-10.0%; Glycol (e.g., Propylene glycol (1,2 and 1,3) 0.0-15.0%; water up to 100%.

Uses: 1) fatty acid glycol ester=pearlizing agent, 2) nonionic surfactant=emulsifier and stabilizer, 3) amphoteric surfactant=co-emulsifier to enhance pearlizing effect, and 4) glycol=emulsifier.

Example 64

Liquid Detergent Comprising Esters Formed from Biologically Derived 1,3-Propanediol Fatty acid glycol ester sulfate (A) (e.g., Lauric acid (ethylene glycol) sulfate sodium salt) 10.0-60.0%; Additional surfactant (B) (anionic, nonionic, cationic, amphoteric, and/or zwitterionic) (e.g., Sodium laureth sulfate) 90.0-40.0%; water up to 100.0%.

Foaming behavior may be tested by, preparing a 10% by weight aqueous surfactant solution (21° dH+1% by weight sebum) and determining the foam volume by Standard DIN 53902, Part 1. Test solutions can be made using weight ratios of A (10.0-60.0%) and B (90.0-40.0%). The fatty acid glycol ester sulfates may exhibit advantageous properties: 1) foam booster for other surfactants, 2) foam stability in the presence of hard water and/or oil, 3) improve formulation of surfactants with poor solubility in cold water, 4) contribute to cleaning performance, 5) dermatologically safe, 6) readily biodegradable, and 7) free of nitosamines.

Example 65

Liquid Detergent Comprising Esters Formed from Biologically Derived 1,3-Propanediol Surfactant (anionic, nonionic, or amphoteric) (e.g., Sodium POE (3) lauryl ether sulfate, Lauryl amidopropylbetaine, Coconut oil fatty acid monothanol amide, and POE (12) lauryl ether) 1.0-50.0%; Fatty acid glycol ester (e.g., Ethylene glycol distearate) 0.3-5.0%; Glyceryl ether (e.g., N-Octyl glyceryl ether) 0.1-10.0%; water up to 100%.

Compositions will have 1) a pearly luster, and 2) are excellent in the dispersion stability of a pearlent.

Procedure—combine all ingredients together, heating the mixture to 80° C. and allowing the ingredients to melt, and then cooling the melt to 30° C. with stirring.

Example 66

Liquid Detergent Comprising Esters Formed from Biologically Derived 1,3-Propanediol Diamine (pKa1 & pKa2 range 8.0-11.5 and molecular weight less-than or equal-to 400 g/mol) (e.g., 1,3-bis(methylamine)-cyclohexane) 0.1-15.0%; Anionic Surfactant (e.g., $C_{12}$-$C_{13}$ alkyl ethoxy sulfonate) 0.5-90.0%; Amphoteric Surfactant (e.g., $C_{12}$-$C_{14}$ amine oxide) 0.10-20.0%; Glycol (e.g., Propylene Glycol) 0.75-25.0%; Optional Ingredients include Polymeric Suds Stabilizer (e.g., (N,N,-dimethylamino)ethyl methacrylate) 0.01-15.0%; Builder (e.g., Citric Acid) 0.50-50.0%; Enzyme(s) (e.g., Alcalase® (Novo Industri A/S) and TERMAMYL® (Novo Industri A/S)) 0.0001-5.0%; Buffer (e.g., Sodium Carbonate) 0.10-10.0%; Alkali Inorganic Salt (e.g., NaCl) 0.01-1.0%: Perfume (e.g., Orange Oil) 0.01-2.0%; Chelating Agents (e.g., Ethylenediaminetetrace-tates) 0.01-15.0%.

Diamines—Improve cleaning performance; Surfactants—Cleaning performance; Glycols—1) Enhanced physical and enzymatic stability, 2) Act as a hydrotrope (phase stabilizer); Suds Stabilizer—Extend suds volume and duration; Builder—Support detergent action; Enzyme—Cleaning performance; Buffer—pH adjustment; Alkali Inorganic Salt—Support detergent action; Perfume—Help remove iron and manganese.

What is claimed:

1. A flavoring agent composition comprising an ester of 1,3-propanediol, wherein the composition is biodegradable, wherein the ester is a monomer and comprises at least 3% biobased carbon, and wherein said composition has a lower anthropogenic $CO_2$ emission profile as compared to a biodegradable composition comprising an ester of 1,3-propanediol with a bio-based carbon content of 0%.

2. The composition of claim 1, wherein the flavoring agent composition further comprises a flavoring oil.

3. The composition of claim 2 wherein the flavoring oil comprises orange oil.

4. The composition of claim 1, wherein the ester has 50% biobased carbon.

5. The composition of claim 1, wherein the ester has 100% biobased carbon.

6. The composition of claim 1, wherein the ester has the formula R1-C(=O)—O—CH2-CH2-CH2-OH, wherein R1 is a linear or branched carbon chain of a length between about 1 and about 40 carbons.

7. The composition of claim 1, wherein the ester has the formula R1-C(=O)—O—CH2-CH2-CH2-O—C(=O)—R2, wherein R1 and R2 are linear or branched carbon chains of a length between about 1 and about 40 carbons.

8. The composition of claim 1, wherein the ester is selected from the group consisting of:
   i. propanediol distearate, monostearate and a mixture thereof;
   ii. propandiol dilaurate, monolaurate and a mixture thereof;
   iii. propanediol dioleate, monooleate and a mixture thereof;
   iv. propanediol divalerate, monovalerate and a mixture thereof;
   v. propanediol dicaprylate, monocaprylate and a mixture thereof;
   vi. propanediol dimyristate, monomyristate and a mixture thereof;
   vii. propanediol dipalmitate, monopalmitate and a mixture thereof;
   viii. propanediol dibehenate, monobehenate and a mixture thereof;
   ix. propanediol adipate;
   x. propanediol maleate;
   xi. propanediol dibenzoate;
   xii. propanediol diacetate; and
   xiii. mixtures thereof.

9. The composition of claim 1, further comprising 1,3-propanediol.

10. The composition of claim 9, wherein the 1,3-propanediol has 50% biobased carbon.

11. The composition of claim 9, wherein the 1,3-propanediol has 100% biobased carbon.

12. A flavoring agent composition comprising 1,3-propanediol, wherein the 1,3-propanediol is biologically derived, wherein the composition is biodegradable and has a lower anthropogenic $CO_2$ emission profile as compared to a biodegradable composition comprising 1,3-propanediol with a bio-based carbon content of 0%, and wherein the 1,3-propanediol is a monomer, and comprises at least 3% biobased carbon.

13. The composition of claim 12, wherein the flavoring agent composition further comprises a flavoring oil.

14. The composition of claim 13 wherein the flavoring oil comprises orange oil.

15. The composition of claim 12, wherein the 1,3-propanediol has 50% biobased carbon.

16. The composition of claim 12, wherein the 1,3-propanediol has 100% biobased carbon.

17. A food, pharmaceutical or medicine composition comprising the composition of claim 1.

18. A food, pharmaceutical or medicine composition comprising the composition of claim 12.

* * * * *